US006919176B2

(12) United States Patent
Yang et al.

(10) Patent No.: US 6,919,176 B2
(45) Date of Patent: Jul. 19, 2005

(54) POLYPEPTIDES AND NUCLEIC ACIDS ASSOCIATED WITH CANCER

(75) Inventors: Jianxin Yang, Commack, NY (US); Songzhu An, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 271 days.

(21) Appl. No.: 09/850,948

(22) Filed: May 7, 2001

(65) Prior Publication Data

US 2003/0059770 A1 Mar. 27, 2003

(51) Int. Cl.[7] ................................................ C12Q 1/68
(52) U.S. Cl. ...................... 435/6; 435/91.1; 435/91.2; 435/94; 536/23.1; 536/24.3; 536/24.31; 536/24.33; 530/350
(58) Field of Search ......................... 435/6, 91.1, 91.2, 435/94; 536/23.1, 24.3, 24.31, 24.33; 530/350

(56) References Cited

U.S. PATENT DOCUMENTS

| 5,912,143 | A | * | 6/1999 | Bandman et al. ........... 435/69.1 |
| 6,221,627 | B1 | * | 4/2001 | Sathe et al. ................. 435/69.1 |

FOREIGN PATENT DOCUMENTS

| WO | WO 96/39442 A1 | 12/1996 |
| WO | WO 98/32858 A2 | 7/1998 |
| WO | WO 00/22129 A1 | 4/2000 |
| WO | WO 00/22131 A2 | 4/2000 |

OTHER PUBLICATIONS

Schmid S et al, 2001, J comparative Neurology, 430(2): 160–71.*
Conner et al, 1996, Mol Brain Res, 42: 1–17.*
Burgess et al. Journal of Cell Biology, 1990, 11: 2129–2138.*
MPSRCH search report, 2002, us–09–850–948–8.rai. pp. 2–3.*
Lazar et al. Molecular and Cell Biology, 1988, 8: 1247–1252.*
Tao. et al. The Journal of Immunology, 1989, 143(8):2595–2601.*
Gillies et al. Human Antibodies and Hybridomas, 1990, 1(1): 47–54.*
Dorland's illustrated Medical dictionary, 26th ed, 1981, p. 455.*
van de Vijver, M et al, 1987, Mol Cell Biol, 7(5): 2019–2023.*
Jansen, M et al, 1995, Pediatric Res, 37 (6): 681–686.*
Alberts et al. Molecular Biology of the Cell, 3rd edition, 1994, p. 465.*
Shantz and Pegg. Int J of Biochem and Cell Biol., 1999, vol. 31, pp. 107–122.*
McClean and Hill. Eur J of Cancer, 1993, vol. 29A, pp. 2243–2248.*
Fu et al. EMBO Journal, 1996, vol. 15, pp. 4392–4401.*
Yokota, J et al. Oncogene, 1988,vol. 3, pp. 471–475.*
Capone, M et al, 1998, Genbank Sequence Database (Accession AAV40374 and MPSRCH search report, 2002, us–09–850–948–7.mg, pp. 5–6.*
An, Songzhu, et al., "Cloning, sequencing and tissue distribution of two related G protein–coupled receptor candidates expressed prominently in human lung tissue," *FEBS Letters* (1995) 375: 121–124.
Kabarowski, Janusz H.S., et al., "Direct genetic demonstration of Gα13 coupling to the orphan G protein–coupled receptor G2A leading to RhoA–dependent actin rearrangement," *PNAS* (2000) 97(22): 12109–12114.
Kyaw, Hia, et al., "Cloning, characterization ,. and mapping of human homolog of mouse T–cell death–associated gene," *DNA and Cell Biology* (1998) 17(6): 493–500.
Mahadevan, Mani S., et al., "Isolation of a novel G protein–coupled receptor (GPR4) localized to chromosome 19q13.1," *Genomics* (1995) 30: 84–88.
Weng, Zhiang, et al., "A DNA damage and stress inducible G protein–coupled receptor blocks cells in G2/M," *Proc. Natl. Acad. Sci. USA* (1998) 95: 12334–12339.
Xu, Yan and Casey, Graham, "Identification of Human OGR1, a novel G protein–coupled receptor that maps to chromosome 14," *Genomics* (1996) 35: 397–402.
Xu, Yan, et al., "Sphingosylphosphorylcholine is a ligand for ovarian cancer G–protein–coupled receptor 1," *Nature Cell Biology* (2000) 2: 261–267.
Zohn, Irene E., et al., "G2A is an oncogenic G protein–coupled receptor," *Oncogene* (2000) 19: 3866–3877.
Im, Dong–Soon, et al, "Identification of a Molecular Target of Psychosine and Its Role in Globoid Cell Formation," *The Journal of Cell Biology* (2001) 153(2); 429–434.
Miller, Jeff F., et al., "Mice Lacking the Orphan G Protein–Coupled Receptor G2A Develop a Late–Onset Autoimmune Syndrome," *Immunity* (May 2001) 14(5); 561–571.

* cited by examiner

*Primary Examiner*—Susan Ungar
*Assistant Examiner*—Minh-Tam Davis
(74) *Attorney, Agent, or Firm*—Townsend and Townsend and Crew LLP

(57) ABSTRACT

The present invention provides methods, reagents, and kits for diagnosing and treating cancer in a mammal, e.g., a human. This invention is based upon the discovery that G2A, GPR4, GPR65, and OGR1 are overexpressed and/or amplified in cancer. Methods to detect cancer or a propensity to develop cancer, to monitor the efficacy of a cancer treatment, and to treat cancer, by inhibiting the expression and/or activity of G2A, GPR4, GPR65, and OGR1 in a cancer cell are included.

12 Claims, 6 Drawing Sheets

G2A, GPR4, GPR65 and OGR1 Activate Various Signaling Pathways in 293 Cells

CREB □    NFAT ■    CRE    SRE

POLYPEPTIDES AND NUCLEIC ACIDS ASSOCIATED WITH CANCER

CROSS-REFERENCES TO RELATED APPLICATIONS

Not applicable.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to the field of cancer diagnosis and treatment. Methods and diagnostic reagents are provided for diagnosing and treating cancers that involve abnormal or abnormally expressed G-Protein-coupled receptors (GPCRS), GPCR2A, GPR4, GPR65, and OGR1.

BACKGROUND OF THE INVENTION

G-protein coupled receptors are cell surface receptors that indirectly transduce extracellular signals to downstream effectors, which can be intracellular signaling proteins, enzymes, or channels, and changes in the activity of these effectors then mediate subsequent cellular events. The interaction between the receptor and the downstream effector is mediated by a G-protein, a heterotrimeric protein that binds GTP. G-protein coupled receptors ("GPCRs") typically have seven transmembrane regions, along with an extracellular domain and a cytoplasmic tail at the C-terminus. These receptors form a large superfamily of related receptor molecules that play a key role in many signaling processes, such as sensory and hormonal signal transduction. The identification of GPCRs that are associated with cancer is important for understanding the normal process of signal transduction as well as its involvement in pathologic processes. For example, GPCRs can be used for diagnostic and prognostic applications as well as for drug discovery. Further identification of GPCRs associated with cancer is therefore of great interest.

SUMMARY OF THE INVENTION

The present invention provides methods, reagents, and kits for detecting and treating cancer. In particular, the invention provides GPCR polypeptide and polynucleotide sequences that are amplified and/or overexpressed in cancer cells. Accordingly, the present methods can be used to detect cancer or a propensity to develop cancer, to monitor the efficacy of a cancer treatment, to identify inhibitors of the GPCRs, and to treat cancer, e.g., by inhibiting the expression and/or activity of the GPCRs in a cancer cell.

In one aspect, the present invention provides a method of detecting tumor tissue in a biological sample from a mammal, the method comprising providing the biological sample from the mammal and detecting an overexpression of a GPCR2A, GPR4, GPR65, or OGR1 polypeptide in the biological sample, thereby detecting tumor tissue in the biological sample.

The method includes an embodiment in which a GPCR2A, GPR4, GPR65, or OGR1 polypeptide is detected using an antibody that selectively binds to GPCR2A, GPR4, GPR65, or OGR1. Often, the amount of GPCR2A, GPR4, GPR65, or OGR1 polypeptide is quantified by immunoassay. In another embodiment, detecting the overexpression of a GPCR2A, GPR4, GPR65, or OGR1 polypeptide comprises detecting the activity of the GPCR2A, GPR4, GPR65, or OGR1 polypeptide.

In an alternative embodiment, detecting overexpression of a GPCR2A, GPR4, GPR65, or OGR polypeptide comprises detecting an mRNA that encodes the GPCR2A, GPR4, GPR65, or OGR polypeptide. Often, the mRNA is detected using an amplification reaction.

In one embodiment, the tumor tissue is from an epithelial tumor, often an ovarian tumor, a colorectal tumor, a breast tumor, a lung tumor, or a prostate tumor. In other embodiments, the mammal is a human and the biological sample is a tissue biopsy, frequently from colorectal tissue, lung tissue, breast tissue, ovarian tissue, or prostate tissue.

In another aspect, the present invention provides a method of detecting the presence of tumor tissue in a biological sample from a mammal, the method comprising providing the biological sample from the mammal and detecting an increase in copy number of a gene encoding a GPCR2A, GPR4, GPR65, or OGR1 in the biological sample, thereby detecting the presence of tumor tissue in the biological sample. In one embodiment, the detecting step comprises contacting the gene with a probe that selectively hybridizes to the gene under conditions in which the probe selectively hybridizes to the gene to form a stable hybridization complex and detecting the hybridization complex. Often, the contacting step includes a step of amplifying the gene in an amplification reaction. In one embodiment, the amplification reaction is a polymerase chain reaction. In other embodiments, the tumor tissue is from an epithelial tumor, often an ovarian tumor, a colorectal tumor, a breast tumor, a lung tumor, or a prostate tumor. In additional embodiments, the mammal is a human and the biological sample is a tissue biopsy, frequently from colorectal tissue, lung tissue, breast tissue, ovarian tissue, or prostate tissue.

In another aspect, the invention provides a method of monitoring the efficacy of a therapeutic treatment of a tumor, the method comprising providing a biological sample from a mammal undergoing the therapeutic treatment, and detecting a level of a GPCR2A, GPR4, GPR65, or OGR1 polynucleotide or polypeptide in the biological sample compared to a level in a biological sample from the mammal prior to, or earlier in, the therapeutic treatment, thereby monitoring the efficacy of the therapy. In one embodiment, the tumor is an epithelial tumor, often a lung, colorectal, breast, ovarian, or prostate tumor. In another embodiment the mammal is a human.

The invention also provides a method of identifying a compound that inhibits the activity of a GPCR2A, GPR4, GPR65, or OGR1 polypeptide, the method comprising contacting the compound with the GPCR2A, GPR4, GPR65, or OGR1 polypeptide and detecting a decrease in the activity of the GPCR2A, GPR4, GPR65, or OGR1 polypeptide. In one embodiment, the polypeptide is linked to a solid phase. In another embodiment, the GPCR2A, GPR4, GPR65, or OGR1 polypeptide is expressed in a cell. Additionally, the GPCR2A, GPR4, GPR65, or OGR1 polypeptide can be amplified in the cell compared to normal.

In another aspect, the invention provides a method of treating a cancer that overexpresses a GPCR2A, GPR4, GPR65, or OGR1, the method comprising the step of contacting a tumor cell with a therapeutically effective amount of an inhibitor of the GPCR2A, GPR4, GPR65, or OGR1. In one embodiment the tumor cell is an epithelial tumor cell, often an ovarian tumor, a colorectal tumor, a breast tumor, a lung tumor, or a prostate tumor. In another embodiment, the inhibitor is identified using a method of identifying a compound that inhibits the activity of a GPCR2A, GPR4, GPR65, or OGR1, the method comprising contacting the compound with the GPCR2A, GPR4, GPR65, or OGR1 and detecting a decrease in the activity of the GPCR2A, GPR4, GPR65, or OGR1. In one embodiment, the inhibitor is an antibody. Alternatively, the inhibitor is an antisense polynucleotide.

DETAILED DESCRIPTION OF THE INVENTION AND PREFERRED EMBODIMENTS

Introduction

Figure 1:
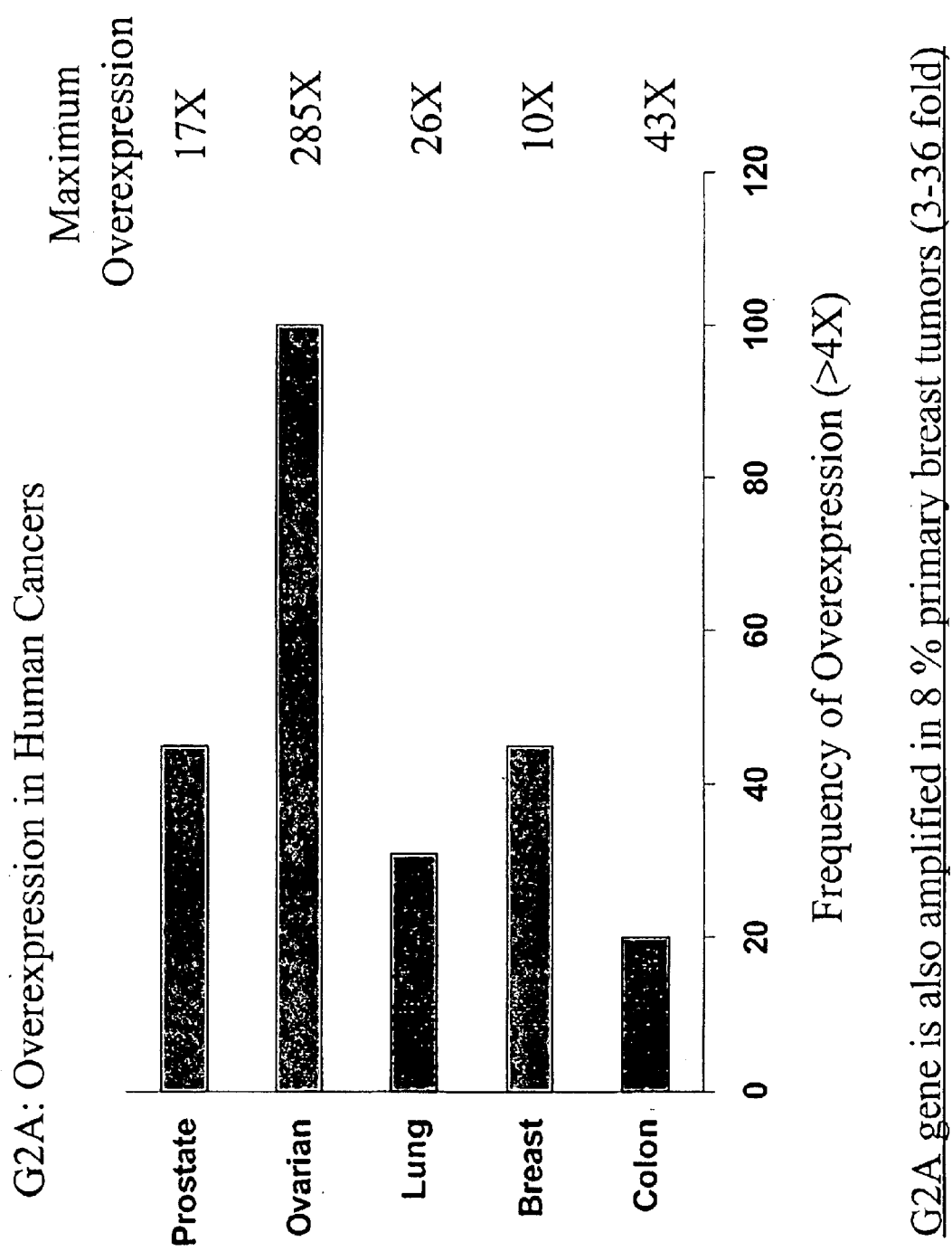
FIG. 1 sets forth exemplary expression data for G2A in primary tumor samples.
Figure 2:
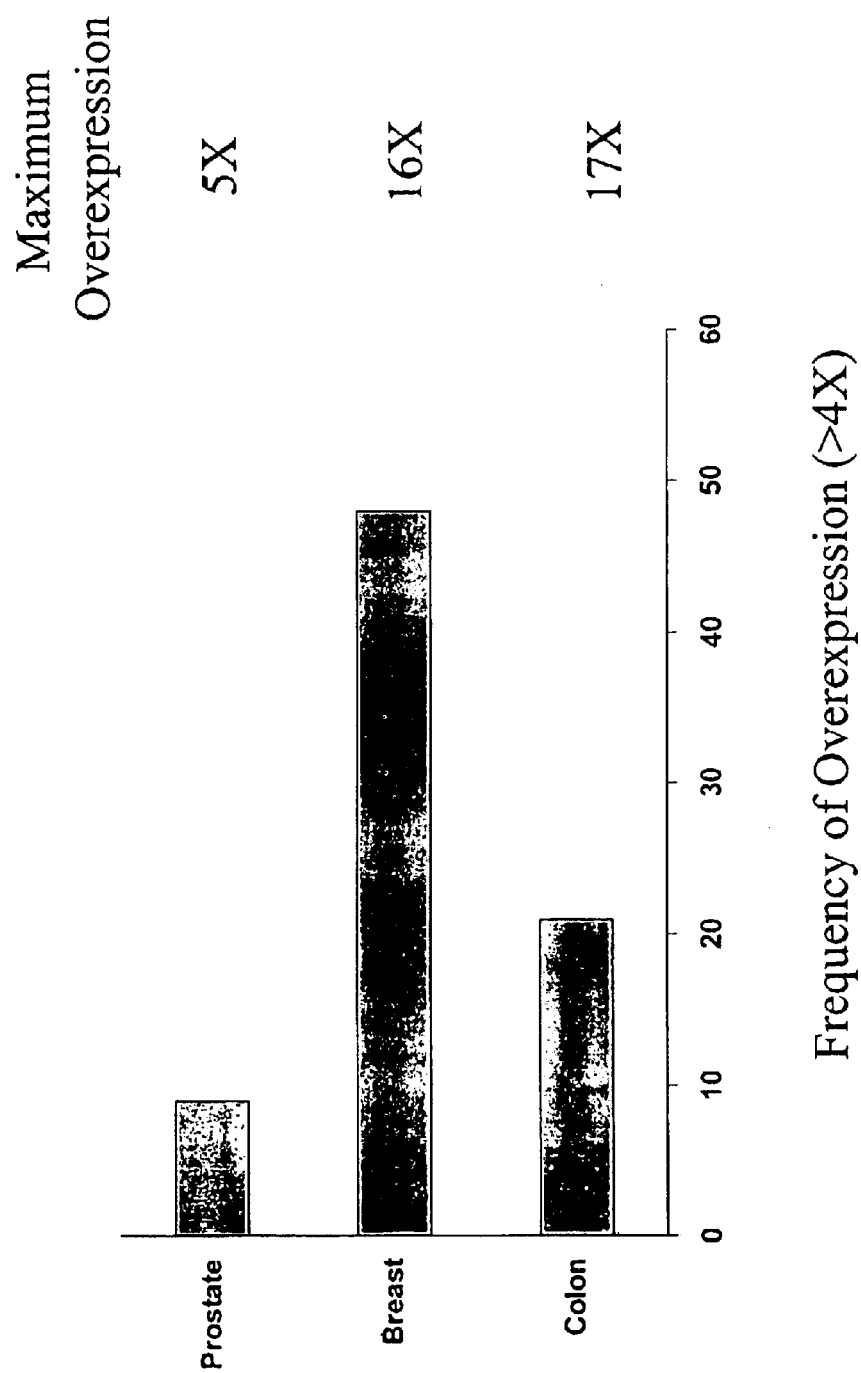
FIG. 2 sets forth exemplary expression data for GPR4 in primary tumor samples.
Figure 3:
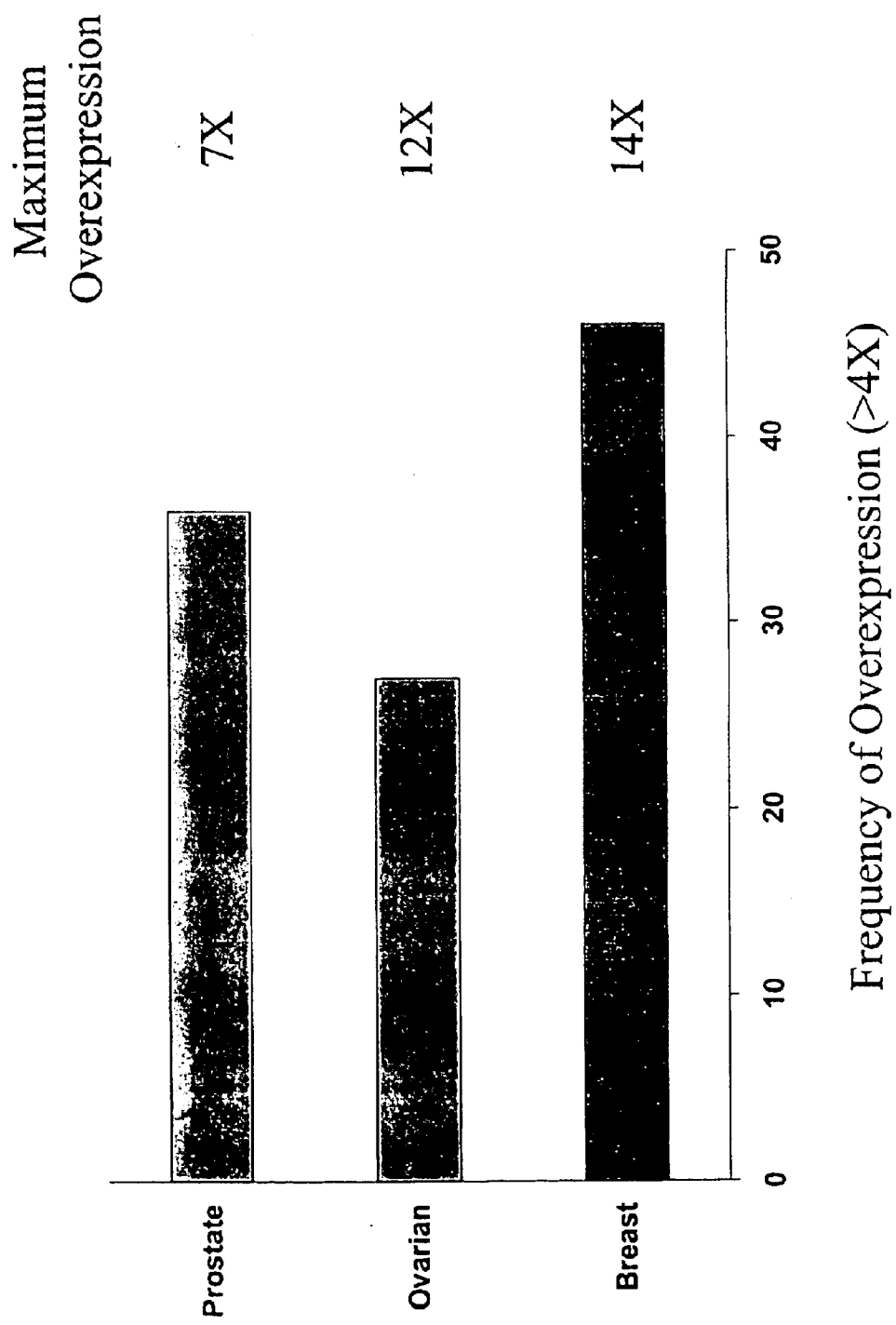
FIG. 3 sets forth exemplary expression data for GPR65 in primary tumor samples.
Figure 4:
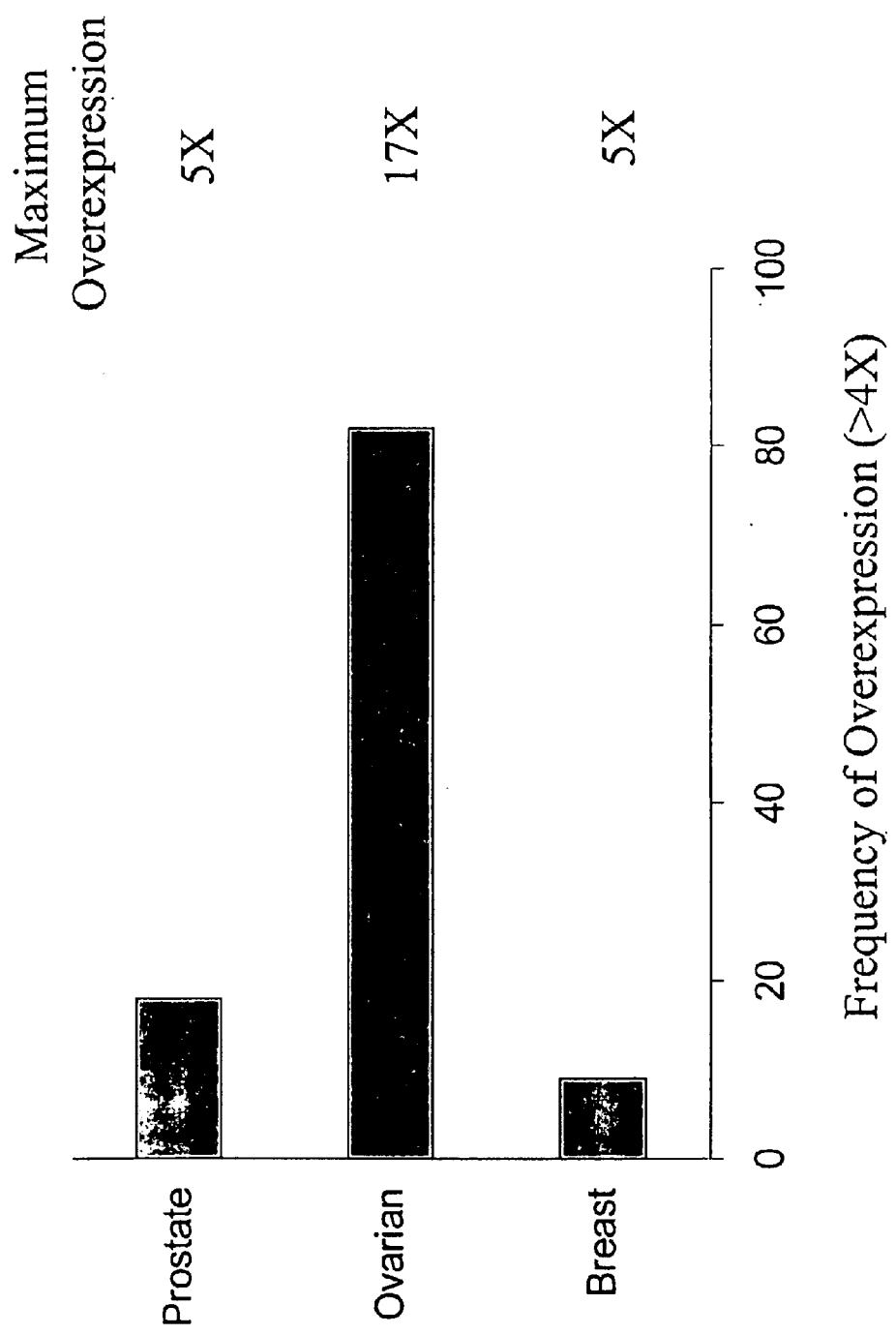
FIG. 4 sets forth exemplary expression data for OGR1 in primary tumor samples.

The present invention provides methods, reagents, and kits for diagnosing and treating cancer. The invention is based upon the discovery that particular GPCR polynucleotide and polypeptides are overexpressed in cancer cells, particularly ovarian, lung, colon, breast, or prostate cancer cells. The nucleic acids and the receptors that they encode are referred individually designated as G2A, GPR4, GPR65, or OGR1.

These GPCRs are components of signal transduction pathways in a variety of cells. Furthermore, G2A (see, e.g., Weng et al., *Proc. Natl. Acad. Sci. USA* 95:12334–12339, 1998) has also been shown to be an oncogene in cell culture (Kabarowski et al., *Proc. Natl. Acad. Sci USA* 97:12109–12114, 2000; Zohn et al., *Oncogene* 19:3866–3877, 2000), i.e., when expressed at high levels in NIH3T3 cells, G2A induced a range of phenotypes characteristic of oncogenic transformation. Nucleic acids encoding GPR4, GPR65, and OGR1 have been previously isolated (see, e.g., Xu and Case, *Genomics* 35:397–402, 1996; An et al., *FEBS Lett.* 375:121–124, 1995; Mahadevan et al., *Genomics* 30:84–88, 1995; Kyaw et al., *DNA Cell Biol.* 17:493–500, 1998; and Xu et al., *Nat. Cell Biol.* 2:261–267, 2000). The three proteins share from about 35–50% identifity with G2A and have been identified in the present invention as oncogenic GPCRs. These three GPCRs also have the ability to activate Rho GTPases, which can induce changes in the structure of the cytoskeleton and can contribute to transformation of a cell.

Accordingly, the present invention provides methods to detect cancer or a propensity to develop cancer, to monitor the efficacy of a cancer treatment, as well as to treat cancer, e.g., by inhibiting the expression and/or activity of G2A, GPR4, GPR65, or OGR1 in a cancer cell. The methods of the invention typically involve detecting the presence G2A, GPR4, GPR65, or OGR1 in a biological sample taken from a mammal. In certain embodiments, a level of G2A, GPR4, GPR65, or OGR1 in a biological sample will be compared with a control sample taken from a cancer-free animal, or, preferably, with a value expected for a sample taken from a cancer-free animal. A control sample can also be obtained from normal tissue from the same mammal that is suspected to have cancer.

The ability to detect cancer cells by virtue of an increased level of G2A, GPR4, GPR65, or OGR1 is useful for any of a large number of applications. For example, an increased level of G2A, GPR4, GPR65, or OGR1 in cells of a mammal can be used, alone or in combination with other diagnostic methods, to diagnose cancer in the mammal or to determine the propensity of a mammal to develop cancer over time. The detection of G2A, GPR4, GPR65, or OGR1 can also be used to monitor the efficacy of a cancer treatment. For example, a level of a G2A, GPR4, GPR65, or OGR1 polypeptide or polynucleotide after an anti-cancer treatment is compared to the level in the mammal before the treatment. A decrease in the level of the G2A, GPR4, GPR65, or OGR1 polypeptide or polynucleotide after the treatment indicates efficacious treatment.

An increased level or diagnostic presence of G2A, GPR4, GPR65, or G2A, GPR4, GPR65, or OGR1 can also be used to influence the choice of anti-cancer treatment in a mammal, where, for example, the level of G2A, GPR4, GPR65, or OGR1 increase directly correlates with the aggressiveness of the anti-cancer therapy. For example, an increased level of G2A, GPR4, GPR65, or OGR1 in tumor cells can indicate that the use of an agent that decreases proliferation would be effective in treating the tumor.

In addition, the ability to detect cancer cells can be useful to monitor the number or location of cancer cells in a patient, in vivo or in vitro, for example, to monitor the progression of the cancer over time. In addition, the level or presence or absence of G2A, GPR4, GPR65, or OGR1 can be statistically correlated with the efficacy of particular anti-cancer therapies or with observed prognostic outcomes, thereby allowing the development of databases based on which a statistically-based prognosis, or a selection of the most efficacious treatment, can be made in view of a particular level or diagnostic presence of G2A, GPR4, GPR65, or OGR1.

The present invention also provides methods for treating cancer. In certain embodiments, the proliferation of a cell with an elevated level of G2A, GPR4, GPR65, or OGR1 polynucleotides, polypeptides, or polypeptide activity is inhibited. The proliferation is decreased by, for example, contacting the cell with an inhibitor of G2A, GPR4, GPR65, or OGR1 transcription or translation, or an inhibitor of the activity of a G2A, GPR4, GPR65, or OGR1 polypeptide. Such inhibitors include, but are not limited to, antisense polynucleotides, ribozymes, antibodies, dominant negative G2A, GPR4, GPR65, or OGR1 polypeptides, and small molecule inhibitors of G2A, GPR4, GPR65, or OGR1 activity.

The present methods can be used to diagnose, determine the prognosis for, or treat, any of a number of types of cancers. In preferred embodiments, the cancer is an epithelial cancer, e.g., colorectal, lung, breast, prostate, ovarian, kidney, stomach, bladder, or any cancer of the gastrointestinal tract.

The diagnostic methods of this invention can be used in animals including, for example, primates, canines, felines, murines, bovines, equines, ovines, porcines, lagomorphs, etc, as well as in humans.

Kits are also provided for carrying out the herein-disclosed diagnostic and therapeutic methods.

Definitions

A "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

The phrase "detecting a cancer" refers to the ascertainment of the presence or absence of cancer in an animal. "Detecting a cancer" can also refer to obtaining indirect evidence regarding the likelihood of the presence of cancerous cells in the animal. Detecting a cancer can be accomplished using the methods of this invention alone, in combination with other methods, or in light of other information regarding the state of health of the animal.

"GPCR," "G2A", "GPR4", "GPR65", and "OGR1" all refer to G-protein coupled receptors, the genes for most of which have been mapped to particular chromosomes and which are overexpressed in cancer. The GPCRs of the invention have seven transmembrane regions and have "G-protein coupled receptor activity," e.g., they bind to G-proteins in response to extracellular stimuli and promote production of second messengers such as $IP_3$, cAMP, and $Ca^{2+}$ via stimulation of downstream effectors such as phospholipase C and adenylate cyclase (for a description of the structure and function of GPCRs, see, e.g., Fong, supra, and Baldwin, supra).

Topologically, GPCRs have an N-terminal "extracellular domain," a "transmembrane domain" comprising seven transmembrane regions and corresponding cytoplasmic and extracellular loops, and a C-terminal "cytoplasmic domain" (see, e.g., Buck & Axel, Cell 65:175–187 (1991)). These domains can be structurally identified using methods known to those of skill in the art, such as sequence analysis programs that identify hydrophobic and hydrophilic domains (see, e.g., Kyte & Doolittle, J. Mol. Biol. 157:105–132 (1982)). Such domains are useful for making chimeric proteins and for in vitro assays of the invention.

"Extracellular domain" therefore refers to the domain of a GPCR that protrudes from the cellular membrane and often binds to an extracellular ligand. This domain is often useful for in vitro ligand binding assays, both soluble and solid phase.

"Transmembrane domain," comprises seven transmembrane regions plus the corresponding cytoplasmic and extracellular loops. Certain regions of the transmembrane domain can also be involved in ligand binding.

"Cytoplasmic domain" refers to the domain of a GPCR that protrudes into the cytoplasm after the seventh transmembrane region and continues to the C-terminus of the polypeptide.

"GPCR activity" refers to the ability of a GPCR to transduce a signal. Such activity can be measured, e.g., in a heterologous cell, by coupling a GPCR (or a chimeric GPCR) to a G-protein and a downstream effector such as PLC, and measuring increases in intracellular calcium (see, e.g., Offermans & Simon, J. Biol. Chem. 270:15175–15180 (1995)). Receptor activity can be effectively measured by recording ligand-induced changes in $[Ca^{2+}]_i$ using fluorescent $Ca^{2+}$-indicator dyes and fluorometric imaging.

The terms "G2A", "GPR4", "GPR65", or "OGR1" refer to G2A, GPR4, GPR65, or OGR1 nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 100, 200, 500, 1000, or more amino acids, to a G2A, GPR4, GPR65, and OGR1 sequence of SEQ ID NO:2; 4, 6, or 8 (2) bind to antibodies, e.g., polyclonal antibodies, raised against an immunogen comprising an amino acid sequence of SEQ ID NO:2,4, 6, or 8 and conservatively modified variants thereof; (3) specifically hybridize under stringent hybridization conditions to a G2A, GPR4, GPR65, and OGR1 nucleic acid sequence of SEQ ID NO:1, 3, 5, or 7 and conservatively modified variants thereof; (4) have a nucleic acid sequence that has greater than about 90%, preferably greater than about 96%, 97%, 98%, 99%, or higher nucleotide sequence identity, preferably over a region of over a region of at least about 50, 100, 200, 500, 1000, or more nucleotides, to SEQ ID NO:1, 3, 5, or 7; or (5) are amplified by primers that specifically hybridize under stringent hybridization conditions to the same sequence as a primer set such as the primers set out in SEQ ID NOs.:9 and 10; 12 and 13; 15 and 16; and 18 and 19, respectively.

The "level of G2A, GPR4, GPR65, and OGR1 mRNA" in a biological sample refers to the amount of mRNA transcribed from an G2A, GPR4, GPR65, and OGR1 gene that is present in a cell or a biological sample. The mRNA generally encodes a functional G2A, GPR4, GPR65, and OGR1 protein, although mutations or microdeletions may be present that alter or eliminate the function of the encoded protein. A "level of G2A, GPR4, GPR65, and OGR1 mRNA" need not be quantified, but can simply be detected, e.g., a subjective, visual detection by a human, with or without comparison to a level from a control sample or a level expected of a control sample.

The "level of G2A, GPR4, GPR65, and OGR1 protein or polypeptide" in a biological sample refers to the amount of polypeptide translated from a G2A, GPR4, GPR65, and OGR1 mRNA that is present in a cell or biological sample. The polypeptide may or may not have G2A, GPR4, GPR65, and OGR1 protein activity. A "level of G2A, GPR4, GPR65, and OGR1 protein" need not be quantified, but can simply be detected, e.g., a subjective, visual detection by a human, with or without comparison to a level from a control sample or a level expected of a control sample.

"Biological sample" as used herein is a sample of biological tissue or fluid that contains nucleic acids or polypeptides of G2A, GPR4, GPR65, and OGR1. Such samples include, but are not limited to, tissue isolated from humans, mice, and rats. Biological samples may also include sections of tissues such as frozen sections taken for histologic purposes. A biological sample is typically obtained from a eukaryotic organism, such as insects, protozoa, birds, fish, reptiles, and preferably a mammal such as a cow, dog, cat, rat, mouse, guinea pig, or rabbit, and most preferably a primate such as chimpanzees or humans.

"Providing a biological sample" means to obtain a biological sample for use in the methods described in this invention. Most often, this will be done by removing a sample of cells from an animal, but can also be accomplished by using previously isolated cells (e.g., isolated by another person, at another time, and/or for another purpose), or by performing the methods of the invention in vivo.

A "control sample" refers to a sample of biological material representative of healthy, cancer-free animals. The level of G2A, GPR4, GPR65, and OGR1 in a control sample, a "control level", is desirably typical of the general population of normal, cancer-free animals. This sample can be removed from an animal expressly for use in the methods described in this invention, or can be any biological material representative of normal, cancer-free animals. A control sample can also be obtained from normal tissue from the animal that has cancer or is suspected of having cancer. A control sample can also refer to an established level of G2A, GPR4, GPR65, and OGR1, representative of the cancer-free population, that has been previously established based on measurements from normal, cancer-free animals. If a detection method is used that only detects G2A, GPR4, GPR65, and OGR1 when a level higher than that typical of a normal, cancer-free animal is present, i.e., an immunohistochemical assay giving a simple positive or negative result, this is considered to be assessing the G2A, GPR4, GPR65, and OGR1 level in comparison to the control level, as the control level is inherent in the assay.

"Overexpression" or an "increased," or "elevated," level of G2A, GPR4, GPR65, and OGR1 refers to a level of G2A, GPR4, GPR65, and OGR1 polynucleotide or polypeptide, that, in comparison with a control level of G2A, GPR4, GPR65, and OGR1, is detectably higher. The method of comparison can be statistical, using quantified values for the level of G2A, GPR4, GPR65, and OGR1, or can be compared using nonstatistical means, such as by a visual, subjective assessment by a human.

A level of G2A, GPR4, GPR65, and OGR1 polypeptide or polynucleotide that is "expected" in a control sample refers to a level that represents a typical, cancer-free sample, and from which an elevated, or diagnostic, presence of G2A, GPR4, GPR65, and OGR1 polypeptide or polynucleotide can be distinguished. Preferably, an "expected" level will be controlled for such factors as the age, sex, medical history, etc. of the mammal, as well as for the particular biological sample being tested.

A "full length" G2A, GPR4, GPR65, and OGR1 protein or nucleic acid refers to a polypeptide or polynucleotide sequence, or a variant thereof, that contains all of the elements normally contained in one or more naturally occurring, wild type G2A, GPR4, GPR65, and OGR1 polynucleotide or polypeptide sequences. It will be recognized, however, that derivatives, homologs, and fragments of G2A, GPR4, GPR65, and OGR1 can be readily used in the present invention.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as E. coli, or eukaryotic cells such as yeast, insect, amphibian, or mammalian cells such as CHO, HeLa, and the like.

"Biological sample" as used herein is a sample of biological tissue or fluid that contains nucleic acids or polypeptides of novel GPCRs. Such samples include, but are not limited to, tissue isolated from humans, mice, and rats. Biological samples may also include sections of tissues such as frozen sections taken for histologic purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans. Preferred tissues typically depend on the known expression profile of the GPCR, and include e.g., normal colon, spleen, kidney, liver, hypothalamus, adipose, or other tissues.

The phrase "functional effects" in the context of assays for testing compounds that modulate GPCR-mediated signal transduction includes the determination of any parameter that is indirectly or directly under the influence of a GPCR, e.g., a functional, physical, or chemical effect. It includes ligand binding, changes in ion flux, membrane potential, current flow, transcription, G-protein binding, gene amplification, expression in cancer cells, GPCR phosphorylation or dephosphorylation, signal transduction, receptor-ligand interactions, second messenger concentrations (e.g., cAMP, cGMP, $IP_3$, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of a GPCR, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, transcriptional activation of GPCRs; ligand binding assays; voltage, membrane potential and conductance changes; ion flux assays; changes in intracellular second messengers such as cAMP and inositol triphosphate (IP3); changes in intracellular calcium levels; neurotransmitter release, and the like.

"Inhibitors," "activators," and "modulators" of GPCRs refer to inhibitory, activating, or modulating molecules identified using in vitro and in vivo assays for signal transduction, e.g., ligands, agonists, antagonists, and their homologs and mimetics. Such modulating molecules, also referred to herein as compounds, include polypeptides, antibodies, amino acids, nucleotides, lipids, carbohydrates, or any organic or inorganic molecule. Inhibitors are compounds that, e.g., bind to, partially or totally block stimulation, decrease, prevent, delay activation, inactivate, desensitize, or down regulate signal transduction, e.g., antagonists. Activators are compounds that, e.g., bind to, stimulate, increase, open, activate, facilitate, enhance activation, sensitize or up regulate signal transduction, e.g., agonists. Modulators include compounds that, e.g., alter the interaction of a polypeptide with: extracellular proteins that bind activators or inhibitors; G-proteins; G-protein alpha, beta, and gamma subunits; and kinases. Modulators also include genetically modified versions of GPCRs, e.g., with altered activity, as well as naturally occurring and synthetic ligands, antagonists, agonists, antibodies, small chemical molecules and the like. Such assays for inhibitors and activators include, e.g., expressing GPCRs in vitro, in cells, or cell membranes, applying putative modulator compounds, and then determining the functional effects on signal transduction, as described above.

Samples or assays comprising GPCRs that are treated with a potential activator, inhibitor, or modulator are compared to control samples without the inhibitor, activator, or modulator to examine the extent of inhibition. Control samples (untreated with inhibitors) are assigned a relative GPCR activity value of 100%. Inhibition of a GPCR is achieved when the GPCR activity value relative to the control is about 80%, preferably 50%, more preferably 25–0%. Activation of a GPCR is achieved when the GPCR activity value relative to the control (untreated with activators) is 110%, more preferably 150%, more preferably 200–500% (i.e., two to five fold higher relative to the control), more preferably 1000–3000% higher.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated GPCR nucleic acid is separated from open reading frames that flank the GPCR gene and encode proteins other than the GPCR. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Biologically active" GPCR refers to a GPCR having signal transduction activity and G protein coupled receptor activity, as described above.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which can be made detectable, e.g., by incorporating a radiolabel into the peptide, and used to detect antibodies specifically reactive with the peptide).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region) when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the complement of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4:72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-GPCR" antibody is an antibody or antibody fragment that specifically binds a polypeptide encoded by a GPCR gene, cDNA, or a subsequence thereof The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a particular GPCR can be selected to obtain only those polyclonal antibodies that are specifically immunoreactive with the GPCR, and not with other proteins, except for polymorphic variants, orthologs, and alleles of the GPCR. This selection may be achieved by subtracting out antibodies that cross-react with GPCR molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background. Antibodies that react only with a particular GPCR ortholog, e.g., from specific species such as rat, mouse, or human, can also be made as described above, by subtracting out antibodies that bind to the same GPCR from another species.

The phrase "selectively associates with" refers to the ability of a nucleic acid to "selectively hybridize" with another as defined above, or the ability of an antibody to "selectively (or specifically) bind to a protein, as defined above.

Isolation of Nucleic Acids Encoding GPCRs

General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

Cloning Methods for the Isolation of Nucleotide Sequences Encoding GPCRs

In general, the nucleic acid sequences encoding GPCRs and related nucleic acid sequence homologs are cloned from cDNA and genomic DNA libraries by hybridization with a probe, or isolated using amplification techniques with oligonucleotide primers. For example, GPCR sequences are typically isolated from mammalian nucleic acid (genomic or cDNA) libraries by hybridizing with a nucleic acid probe, the sequence of which can be derived from SEQ ID NOS:1, 3, 5, or 7.

Amplification techniques using primers can also be used to amplify and isolate GPCR nucleic acids from DNA or RNA (see, e.g., section "detection of GPCR polynucleotides", below). Examples of suitable primers for amplification of specific GPCRs include those set forth in the Example Section (see, e.g., Dieffenfach & Dveksler, *PCR Primer: A Laboratory Manual* (1995)). These primers can be used, e.g., to amplify either the full length sequence or a probe, typically varying in size from ten to several hundred nucleotides, which is then used to identify GPCR polynucleotides.

Nucleic acids encoding the GPCRs described herein can also be isolated from expression libraries using antibodies as probes. Such polyclonal or monoclonal antibodies can be raised using the sequence of SEQ ID NOs:2, 4, 6, or 8.

GPCR polymorphic variants, alleles, and interspecies homologs that are substantially identical to a GPCR can be isolated using GPCR nucleic acid probes, and oligonucleotides under stringent hybridization conditions, by screening libraries. Alternatively, expression libraries can be used to clone GPCRs and GPCR polymorphic variants, alleles, and interspecies homologs, by detecting expressed homologs immunologically with antisera or purified antibodies made against GPCRs, which also recognize and selectively bind to the GPCR homolog.

Synthetic oligonucleotides can be used to construct recombinant GPCR genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the GPCR nucleic acid. The specific subsequence is then ligated into an expression vector.

The nucleic acid encoding a GPCR is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising GPCRs or domains thereof can be made according to standard techniques. For example, a domain such as ligand binding domain, an extracellular domain, a transmembrane domain (e.g., one comprising seven transmembrane regions and corresponding extracellular and cytosolic loops), the transmembrane domain and a cytoplasmic domain, an active site, a subunit association region, etc., can be covalently linked to a heterologous protein. For example, an extracellular domain can be linked to a heterologous GPCR transmembrane domain, or a heterologous GPCR extracellular domain can be linked to a transmembrane domain. Other heterologous proteins of choice include, e.g., green fluorescent protein, luciferase, or β-gal.

Detection of GPCR Polynucleotides

Typically, the cancer-associated GPCR polynucleotides or polypeptides detected herein will be at least about 70% identical, and preferably 75%, 80%, 85%, 90%, 91%, 92%, 93%, 94%, 95%, 96%, 97%, 98%, 99% or more identical, over a region of at least about 50, 100, 200, or more nucleotides, or 20, 50, 100, or more amino acids, to SEQ ID NOs 1 or 2 (GPR4), SEQ ID NOs:3 or 4 (GPR65), SEQ ID NOs 5 or 6 (OGR1), or SEQ ID NOs: 7 or 8 (G2A), or to one or more of the sequences available, e.g., from GenBank (see, e.g., human G2A sequences NM_013345 and AF083955, and *M. musculus* NM_019925 and AF083442; human GPR4 sequences XM_009140, NM_005282, U21051, and L36148; human GPR65 sequences XM_007392 and NM_003608; and human OGR1 sequences XM_007383, NM_003485, and U48405).

Such polynucleotides or polypeptides can represent functional or nonfunctional forms of the cancer-associated polynucleotide or polypeptide, or any variant, derivative, or fragment thereof.

Typically, the level and/or presence of cancer-associated polynucleotides or polypeptides will be detected in a biological sample. A "biological sample" refers to a cell or population of cells or a quantity of tissue or fluid from an animal. Most often, the sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure the cancer-associated polynucleotide or polypeptide levels. Numerous types of biological samples can be used in the present invention, including, but not limited to, a tissue biopsy, a blood sample, a buccal scrape, a saliva sample, or a nipple discharge.

As used herein, a "tissue biopsy" refers to an amount of tissue removed from an animal for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

Detection of Copy Number

In one embodiment, the presence of cancer is evaluated by determining the copy number of cancer-associated genes, i.e., the number of DNA sequences in a cell encoding a GPCR cancer-associated protein described herein, for example G2A. Generally, for a given autosomal gene, an animal has two copies of each gene. The copy number can be increased, however, by gene amplification or duplication, e.g., in cancer cells, or reduced by deletion. Methods of evaluating the copy number of a particular gene are well known to those of skill in the art, and include, inter alia, hybridization and amplification based assays.

Hybridization-Based Assays

Any of a number of hybridization based assays can be used to detect the copy number of cancer-associated GPCRs in the cells of a biological sample. One such method is by Southern blot. In a Southern blot, genomic DNA is typically fragmented, separated electrophoretically, transferred to a membrane, and subsequently hybridized to a cancer-associated polynucleotide-specific probe. Comparison of the intensity of the hybridization signal from the probe for the target region with a signal from a control probe for a region of normal genomic DNA (e.g., a nonamplified portion of the same or related cell, tissue, organ, etc.) provides an estimate of the relative copy number of the cancer-associated gene. Southern blot methodology is well known in the art and is described, e.g., in Ausubel et al., or Sambrook et al., supra.

An alternative means for determining the copy number of cancer-associated GPCRs in a sample is by in situ hybridization, e.g., fluorescence in situ hybridization, or FISH. In situ hybridization assays are well known (e.g., Angerer (1987) Meth. Enzymol 152:649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments.

The probes used in such applications are typically labeled, e.g., with radioisotopes or fluorescent reporters. Preferred probes are sufficiently long, e.g., from about 50, 100, or 200 nucleotides to about 1000 or more nucleotides, so as to specifically hybridize with the target nucleic acid(s) under stringent conditions.

In numerous embodiments, "comparative probe" methods, such as comparative genomic hybridization (CGH), are used to detect GPCR gene amplification. In comparative genomic hybridization methods, a "test" collection of nucleic acids is labeled with a first label, while a second collection (e.g., from a healthy cell or tissue) is labeled with a second label. The ratio of hybridization of the nucleic acids is determined by the ratio of the first and second labels binding to each fiber in an array. Differences in the ratio of the signals from the two labels, e.g., due to gene amplification in the test collection, is detected and the ratio provides a measure of the GPCR gene copy number.

Hybridization protocols suitable for use with the methods of the invention are described, e.g., in Albertson (1984) EMBO J. 3: 1227–1234; Pinkel (1988) Proc. Natl. Acad. Sci. USA 85: 9138–9142; EPO Pub. No. 430,402; Methods in Molecular Biology, Vol. 33: In Situ Hybridization Protocols, Choo, ed., Humana Press, Totowa, N.J. (1994), etc.

Amplification-Based Assays

In another embodiment, amplification-based assays are used to measure the copy number of the GPCRs. In such an assay, the G2A, GPR4, GPR65, or OGR1 nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the copy number of the cancer-associated gene. Methods of quantitative amplification are well known to those of skill in the art. Detailed protocols for quantitative PCR are provided, e.g., in Innis et al. (1990) PCR Protocols, A Guide to Methods and Applications, Academic Press, Inc. N.Y.). The known nucleic acid sequences for G2A, GPR4, GPR65, or OGR1 (see, e.g., SEQ ID NO:1, 3, 5, and 7) is sufficient to enable one of skill to routinely select primers to amplify any portion of the gene.

In preferred embodiments, a TaqMan based assay is used to quantify the cancer-associated polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer, e.g., www2.perkin-elmer.com).

Other suitable amplification methods include, but are not limited to, ligase chain reaction (LCR) (see, Wu and Wallace (1989) Genomics 4: 560, Landegren et al. (1988) Science 241: 1077, and Barringer et al. (1990) Gene 89: 117), transcription amplification (Kwoh et al. (1989) Proc. Natl. Acad. Sci. USA 86: 1173), self-sustained sequence replication (Guatelli et al. (1990) Proc. Nat. Acad. Sci. USA 87: 1874), dot PCR, and linker adapter PCR, etc.

Detection of mRNA Expression

Direct Hybridization-Based Assays

Methods of detecting and/or quantifying the level of cancer-associated GPCR gene transcripts (mRNA or cDNA made therefrom) using nucleic acid hybridization techniques are known to those of skill in the art (see, Sambrook et al., (1989) Molecular Cloning: A Laboratory Manual, 2d Ed., vols 1–3, Cold Spring Harbor Press, New York). For example, one method for evaluating the presence, absence, or quantity of GPCR polynucleotides involves a Northern blot: mRNA is isolated from a given biological sample, electrophoresed and transferred from the gel to a nitrocellulose membrane. Labeled GPCR probes are then hybridized to the membrane to identify and/or quantify the mRNA.

Amplification-Based Assays

In another embodiment, a GPCR transcript is detected using amplification-based methods (e.g., RT-PCR). RT-PCR methods are well known to those of skill (see, e.g., Ausubel et al., supra). Preferably, quantitative RT-PCR, e.g., a Taqman assay, is used, thereby allowing the comparison of the level of mRNA in a sample with a control sample or value.

Gene expression of GPCRs can also be analyzed by techniques known in the art, e.g., dot blotting, in situ hybridization, RNase protection, probing DNA microchip arrays, and the like. In one embodiment, high density oligonucleotide analysis technology (e.g., GeneChip™) is used to identify homologs and polymorphic variants of the GPCRs of the invention. In the case where the homologs being identified are linked to a known disease, they can be used with GeneChip™ as a diagnostic tool in detecting the disease in a biological sample, see, e.g., Gunthand et al, AIDS Res. Hum. Retroviruses 14: 869–876 (1998); Kozal et al., Nat. Med. 2:753–759 (1996); Matson et al., Anal Biochem. 224:110–106 (1995); Lockhart et al., Nat. Biotechnol. 14:1675–1680 (1996); Gingeras et al., Genome Res. 8:435–448 (1998); Hacia et al., Nucleic Acids Res. 26:3865–3866 (1998).

Expression in Prokaryotes and Eukaryotes

To obtain high level expression of a cloned gene or nucleic acid, such as those cDNAs encoding GPCRs, one typically subclones a GPCR into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the GPCR protein are available in, e.g., E. coli, Bacillus sp., and Salmo-

*nella* (Palva et al., *Gene* 22:229–235 (1983); Mosbach et al., *Nature* 302:543–545 (1983)). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the GPCR encoding nucleic acid in host cells. A typical expression cassette thus contains a promoter operably linked to the nucleic acid sequence encoding a GPCR and signals required for efficient polyadenylation of the transcript, ribosome binding sites, and translation termination. The nucleic acid sequence encoding a GPCR may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a GPCR-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of GPCR protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a GPCR.

After the expression vector is introduced into the cells, the transfected cells are cultured under conditions favoring expression of a GPCR, which is recovered from the culture using standard techniques (see, e.g., Scopes, *Protein Purification: Principles and Practice* (1982); U.S. Pat. No. 4,673,641; Ausubel et al., supra; and Sambrook et al., supra).

Immunological Detection of GPCRs

In addition to the detection of GPCR genes and gene expression using nucleic acid hybridization technology, one can also use immunoassays to detect GPCRs, e.g., to identify cells such as cancer cells that overexpress the GPCRs. Immunoassays can be used to qualitatively or quantitatively analyze GPCRs. A general overview of the applicable technology can be found in Harlow & Lane, *Antibodies: A Laboratory Manual* (1988).

A. Antibodies to GPCRs

Methods of producing polyclonal and monoclonal antibodies that react specifically with GPCRs are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). Such antibodies can be used for therapeutic and diagnostic applications, e.g., in the treatment and/or detection of any of the GPCR-associated diseases or conditions described herein.

A number of GPCRs comprising immunogens may be used to produce antibodies specifically reactive with GPCRs. For example, a recombinant GPCR or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the GPCR. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-GPCR proteins or even other related proteins from other organisms, using a competitive binding immunoassay. Specific polyclonal antisera and monoclonal antibodies will usually bind with a $K_d$ of at least about 0.1 mM, more usually at least about 1 $\mu$M, optionally at least about 0.1 $\mu$M or better, and optionally 0.01 $\mu$M or better.

Once GPCR specific antibodies are available, GPCRs can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

GPCRs can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the GPCR or antigenic subsequence thereof). The antibody (e.g., anti-GPCR) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled GPCR polypeptide or a labeled anti-GPCR antibody. Alternatively, the labeling agent may be a third moiety, such a secondary antibody, that specifically binds to the antibody/GPCR complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting GPCRs in samples may be either competitive or noncompetitive. Noncompetitive immunoassays are assays in which the amount of antigen is directly measured. In one preferred "sandwich" assay, for example, the anti-GPCR antibodies can be bound directly to a solid substrate on which they are immobilized. These immobilized antibodies then capture GPCRs present in the test sample. The GPCR is thus immobilized is then bound by a labeling agent, such as a second GPCR antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of GPCR present in the sample is measured indirectly by measuring the amount of a known, added (exogenous) GPCR displaced (competed away) from an anti-GPCR antibody by the unknown GPCR present in a sample. In one competitive assay, a known amount of GPCR is added to a sample and the sample is then contacted with an antibody that specifically binds to the GPCR. The amount of exogenous GPCR bound to the antibody is inversely proportional to the concentration of GPCR present in the sample. In a particularly preferred embodiment, the antibody is immobilized on a solid substrate. The amount of GPCR bound to the antibody may be determined either by measuring the amount of GPCR present in a GPCR/antibody complex, or alternatively by measuring the amount of remaining uncomplexed protein. The amount of GPCR may be detected by providing a labeled GPCR molecule.

A hapten inhibition assay is another preferred competitive assay. In this assay the known GPCR, is immobilized on a solid substrate. A known amount of anti-GPCR antibody is added to the sample, and the sample is then contacted with the immobilized GPCR. The amount of anti-GPCR antibody bound to the known immobilized GPCR is inversely proportional to the amount of GPCR present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein at least partially encoded by SEQ ID NOs:1, 3, 5, or 7 can be immobilized to a solid support. Proteins (e.g., GPCR proteins and homologs) are added to the assay that compete for binding of the antisera to the immobilized antigen. The ability of the added proteins to compete for binding of the antisera to the immobilized protein is compared to the ability of GPCRs encoded by SEQ ID NO:1, 3, 5, or 7 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a GPCR, to the immunogen protein (i.e., the GPCR of SEQ ID NOS:2, 4, 6, or 8). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NOS:1, 3, 5, or 7 that is required to inhibit 50% of binding, then the second protein is said to specifically bind to the polyclonal antibodies generated to a GPCR immunogen.

Other Assay Formats

Western blot (immunoblot) analysis is used to detect and quantify the presence of GPCR in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind GPCR. The anti-GPCR antibodies specifically bind to the GPCR on the solid support. These antibodies may be directly labeled or alternatively may be subsequently detected using labeled antibodies (e.g., labeled sheep anti-mouse antibodies) that specifically bind to the anti-GPCR antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g. $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize GPCRs, or secondary antibodies that recognize anti-GPCR.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Diagnosing Cancer

The present methods can be used in the diagnosis, prognosis and treatment of a number of types of cancers. In preferred embodiments, cancers such as epithelial-derived cancers will be diagnosed and/or treated, e.g., breast, ovarian, prostate, lung, and colorectal cancer. Other epithelial cancers include, e.g., kidney, stomach, and bladder cancers. A cancer at any stage of progression can be detected, such as primary, metastatic, and recurrent cancers. Information regarding numerous types of cancer can be found, e.g., from the American Cancer Society (www.cancer.org), or from, e.g., Wilson et al. (1991) Harrison's Principles of Internal Medicine, 12$^{th}$ Edition, McGraw-Hill, Inc.

The present invention provides numerous methods for determining whether or not a mammal has cancer, whether or not a biological sample contains cancerous cells, estimating the likelihood of a mammal developing cancer, and monitoring the efficacy of anti-cancer treatment in a mammal with cancer. Such methods are based on the discovery that cancer cells have an elevated level of G2A, GPR4, GPR65, or OGR1 polynucleotide (i.e., gene copy number and/or mRNA) and/or polypeptide. Accordingly, by determining whether or not a cell contains elevated levels of G2A, GPR4, GPR65, or OGR1 polynucleotide or polypeptide, it is possible to determine whether or not the cell is cancerous. Further, the presence of cancerous cells can be determined indirectly, e.g., in certain embodiments a biological sample that does not itself contain cancerous cells, but which has been taken from an animal with cancerous cells elsewhere in its body, may contain elevated levels of G2A, GPR4, GPR65, or OGR1 reflecting the presence of the cancerous cells.

In numerous embodiments of the present invention, the level and/or presence of G2A, GPR4, GPR65, or OGR1 polynucleotide or polypeptide will be detected in a biological sample, thereby detecting the presence or absence of cancerous cells in the biological sample, or, in certain embodiments, in the mammal from which the biological sample was removed. In preferred embodiments, the biological sample will comprise a tissue sample from a tissue suspected of containing cancerous cells. For example, in an individual suspected of having colon cancer, colorectal tissue is removed. Often, such methods will be used in conjunction with additional diagnostic methods, e.g., detection of other cancer markers, coloscopy, etc. In other embodiments, a tissue sample known to contain cancerous cells, e.g., from a tumor, will be analyzed for G2A, GPR4, GPR65, or OGR1 levels to determine information about the cancer, e.g., the efficacy of certain treatments, the survival expectancy of the animal, etc.

The amount of G2A, GPR4, GPR65, or OGR11 polynucleotide or polypeptide that will indicate the presence of a cancer will depend on numerous factors, including the type of cancer, the age, sex, medical history, etc., of the patient, the cell type, the assay format, etc. In some embodiments, a level of G2A, GPR4, GPR65, or OGR1 in a biological sample will not be quantified or directly compared with a control sample, but will rather be detected relative to a "diagnostic presence" of G2A, GPR4, GPR65, or OGR1 wherein a "diagnostic presence" refers to an amount of G2A, GPR4, GPR65, or OGR1 polynucleotide or polypeptide that indicates the presence of cancer, or indicates a likelihood of cancer, in the mammal from which the sample was taken. Preferably, a "diagnostic presence" will be detectable in a simple assay giving a positive or negative result, where a positive "detection" of a "diagnostic presence" of G2A, GPR4, GPR65, or OGR1 polynucleotide or polypeptide indicates the presence of cancer in the mammal.

The G2A, GPR4, GPR65, or OGR1 level need not be quantified for a "diagnostic presence" to be detected. Rather any method of determining whether G2A, GPR4, GPR65, or OGR1 is present at levels higher than in a normal, cancer-free cell, sample, or mammal may be used. In addition, a "diagnostic presence" does not refer to any absolute quantity of G2A, GPR4, GPR65, or OGR1, but rather on an amount that, depending on the biological sample, cell type, assay conditions, medical condition of the mammal, etc., is sufficient to distinguish the level in a cancerous, or pre-cancerous sample, from a normal, cancer-free sample.

Such methods can be practiced regardless of whether any G2A, GPR4, GPR65, or OGR1 polynucleotide or polypeptide is normally present, or "expected" to be present, in a particular control sample. For example, G2A, GPR4, GpR65, or OGR1 may not be expressed in certain cell types, resulting in a complete absence of G2A, GPR4, GPR65, or OGR1 in a control biological sample consisting of such cell types. For such biological sample, a "diagnostic presence" refers to any detectable amount of G2A, GPR4, GPR65, or OGR1, using any assay. In other tissues, however, there may be a detectable level of G2A, GPR4, GPR65, or OGR1 present in normal, cancer-free cells, and a "diagnostic presence" represents a level that is higher than the normal level, preferably representing a "statistically significant" increase over the normal level. Often, a "diagnostic presence" of G2A, GPR4, GPR65, or OGR1 polynucleotide, polypeptide, and/or protein activity in a biological sample will be at least about 1.5, 2, 5, 10, or more fold greater than a level expected in a sample taken from a normal, cancer-free mammal.

Further, the present methods can be used to assess the efficacy of a course of treatment. For example, in a mammal with cancer from which a biological sample has been found to contain an elevated amount of G2A, GPR4, GPR65, or OGR1 polynucleotide or polypeptide, the efficacy of an anti-cancer treatment can be assessed by monitoring, over time, G2A, GPR4, GPR65, or OGR1 levels. For example, a reduction in G2A, GPR4, GPR65, or OGR1 polynucleotide or polypeptide levels in a biological sample taken from a mammal following a treatment, compared to a level in a sample taken from the mammal before, or earlier in, the treatment, indicates efficacious treatment.

The methods detecting cancer can comprise the detection of one or more cancer-associated polynucleotide or polypeptides sequences. Accordingly, G2A, GPR4, GPR65, or OGR1 can be used either alone or in any combination for the diagnosis or prognosis of cancer. Moreover, G2A, GPR4, GPR65, or OGR1, either alone or in any combination, can be used in conjunction with other cancer-associated sequences to detect cancer.

Determining a Prognosis

The level of G2A, GPR4, GPR65, or OGR1 can be used to determine the prognosis of a mammal with cancer. For example, if cancer is detected using a technique other than by detecting G2A, GPR4, GPR65, or OGR1, e.g., tissue biopsy, then the presence or absence of G2A, GPR4, GPR65, or OGR1 can be used to determine the prognosis for the mammal, i.e., an elevated level of G2A, GPR4, GPR65, or OGR1 will indicate a reduced survival expectancy in the mammal compared to in a mammal with cancer but with a normal level of G2A, GPR4, GPR65, or OGR1P. As used herein, "survival expectancy" refers to a prediction regarding the severity, duration, or progress of a disease, condition, or any symptom thereof. In a preferred embodiment, an increased level, a diagnostic presence, or a quantified level, of G2A, GPR4, GPR65, or OGR1 is statistically correlated with the observed progress of a disease, condition, or symptom in a large number of mammals, thereby providing a database wherefrom a statistically-based prognosis can be made. For example, in a particular type of mammal, i.e., a human of a particular age, gender, medical condition, medical history, etc., a detection of a level of G2A, GPR4, GPR65, or OGR1 that is, e.g., 2 fold higher than a control level may indicate, e.g., a 10% reduced survival expectancy in the human compared to in a similar human with a normal level of G2A, GPR4, GPR65, or OGR1, based on a previous study of the level of G2A, GPR4, GPR65, or OGR1 in a large number of similar patients whose disease progression was observed and recorded.

The methods of the present invention can be used to determine the optimal course of treatment in a mammal with cancer. For example, the presence of an elevated level of G2A, GPR4, GPR65, or OGR1 can indicate a reduced survival expectancy of a mammal with cancer, thereby indicating a more aggressive treatment for the mammal. In addition, a correlation can be readily established between levels of G2A, GPR4, GPR65, or OGR1, or the presence or absence of a diagnostic presence of G2A, GPR4, GPR65, or OGR1, and the relative efficacy of one or another anti-cancer agent. Such analyses can be performed, e.g., retrospectively, i.e., by detecting G2A, GPR4, GPR65, or OGR1 levels in samples taken previously from mammals that have subsequently undergone one or more types of anti-cancer therapy, and correlating the G2A, GPR4, GPR65, or OGR1 levels with the known efficacy of the treatment.

Treating Cancer

The present invention provides numerous methods for treating a mammal with cancer. In addition to allowing the determination of an optimal treatment for a mammal with cancer, as described supra, methods are provided for treating a cancer by inhibiting the growth, proliferation, or steroid hormone production of cells within the mammal, e.g., cancer cells. Typically, the methods are directed at reducing the level of cancer-associated polypeptides, polynucleotides, or protein activity, for example, G2A, GPR4, GPR65, and OGR1, in a cancerous cell. It will be appreciated that more than one of the methods described infra can be performed on a given animal, and may also be administered in conjunction with one or more traditional, well known anti-cancer therapies, e.g., chemotherapy, radiation therapy, surgery, hormone therapy, immunotherapy, etc.

According to the present invention, a "method of treating cancer" refers to a procedure or course of action that is designed to reduce or eliminate the number of cancer cells in an animal, or to alleviate the symptoms of a cancer. "A method of treating cancer" does not necessarily mean that the cancer cells will, in fact, be eliminated, that the number of cells will, in fact, be reduced, or that the symptoms of a cancer will, in fact, be alleviated. Often, a method of treating cancer will be performed even with a low likelihood of success, but which, given the medical history and estimated survival expectancy of an animal, is nevertheless deemed an overall beneficial course of action.

In certain embodiments, the present invention provides methods for treating cancer by detecting the level and/or a diagnostic presence of G2A, GPR4, GPR65, or OGR1 polynucleotide or polypeptide in a biological sample, and, when a diagnostic presence or increased level is detected, administering one or more anti-cancer therapies, including, but not limited to, chemotherapy, radiation therapy, surgery, immunotherapy, hormone therapy, and gene therapy.

One commonly applied anti-cancer therapy is chemotherapy, i.e., the administration of chemical compounds to a mammal with cancer that is aimed at killing or reducing the number of cancer cells within the mammal. Generally, chemotherapeutic agents arrest the growth of or kill cells that are dividing or growing, such as cancer cells. Examples of chemotherapeutic agents include, but are not limited to, genistein, taxol, busulfan, cisplatin, cyclophosphamide (cytoxan), dacarbazine, ifosfamide, mechlorethamine (mustargen), melphalan, carmustine, lomustine, 5-fluorouracil, methotrexate, gemcitabine, cytarabine (Ara-C), fludarabine, bleomycin, dactinomycin, daunorubicin, doxorubicin (Adriamycin), idarubicin, paclitaxel, docetaxel, etoposide, vinblastine, vincristine, vinorelbine, L-asparaginase, amsacrine, tretinoin, and irinotecan.

Another commonly applied anti-cancer therapy is radiation therapy, wherein radioactivity is administered to a mammal with cancer. Radiation kills or inhibits the growth of dividing cells, such as cancer cells. The administration of radiation may be from an external source (e.g., a gamma source, a proton source, a molecular beam source, etc.), or may be through an implantable radioactive material, or a radioactive molecule such as an antibody.

In numerous embodiments, a tissue found to be cancerous using the present methods will be removed using surgery, i.e., the direct removal or ablation of cells, e.g., cancer cells, from a mammal. Most often, the cancer cells will be in the form of a tumor (e.g., a mammary tumor), which is removed from the mammal. The surgical methods may involve removal of healthy as well as cancerous tissue.

Hormone therapy can also be used to treat cancers, e.g., breast cancer. For example, compounds can be administered to a patient that counteract or inhibit hormones, such as estrogen or androgen, that have a mitogenic effect on cells and which often act to increase the cancerous properties of cancer cells in vivo. Hormone therapy can also include methods of reducing or eliminating the production of hormones in an animal, e.g., the surgical removal of ovaries in an animal to prevent estrogen production.

In certain embodiments, immunotherapy will be used to treat a cancer following a diagnosis based on detection of G2A, GPR4, GPR65, or OGR1, i.e., methods of enhancing the ability of an animal's immune system to destroy cancer cells within the animal. Numerous such methods are well known to those of skill in the art. This can involve the treatment with polyclonal or monoclonal antibodies (e.g., Herceptin for treating breast cancer) that bind to particular molecules located on, produced by, or indicative of, tumor cells. Immunotherapeutic methods are well know to those of skill in the art (see, e.g., Pastan et al.(1992) *Ann. Rev. Biochem.*, 61: 331–354, Brinkman and Pastan (1994) *Biochimica Biphysica Acta,* 1198: 27–45, etc.).

In other embodiments, gene therapy will be used to treat a cancer diagnosed based on a detection of G2A, GPR4, GPR65, or OGR1. In such embodiments, a nucleic acid is introduced into cells, e.g., cancer cells, to provide treatment for the cancer. G2A, GPR4, GPR65, or OGR1 expression can be targeted or other cancer-associated genes can be targeted. For example, tumor suppressor genes that are often missing or mutated in a cancer cell, e.g., p53, RB, p21, p16, and others, can be replaced or overexpressed by introducing a nucleic acid encoding a functional gene into the cells. In addition, genes whose overexpression or increased activity contributes to cancer, e.g., ras, telomerase, etc., can be inhibited by any of a number of methods, including, but not limited to, antisense, ribozymes, and polynucleotides encoding dominant negative forms or other inhibiting polypeptides. Such nucleic acids can be delivered using any of a variety of methods, e.g., liposomal formulations, viral vectors, naked DNA injection, etc., and can be performed in vivo or ex vivo.

In preferred embodiments, this invention provides methods of treating a cancer by reducing G2A, GPR4, GPR65, or OGR1 levels in a cell. Typically, such methods are used to reduce an elevated level of G2A, GPR4, GPR65, or OGR1, e.g., an elevated level in a cancerous cell, and can be performed in any of a number of ways, e.g., lowering the copy number of the G2A, GPR4, GPR65, or OGR1 gene or decreasing the level of G2A, GPR4, GPR65, or OGR1 mRNA, protein, or protein activity in a cell. Preferably, the level of G2A, GPR4, GPR65, or OGR1 activity is lowered to a level typical of a normal, cancer-free cell, but the level may be reduced to any level that is sufficient to decrease the proliferation or steroid production of the cell, including to levels above or below those typical of normal cells. Preferably, such methods involve the use of inhibitors of G2A, GPR4, GPR65, or OGR1, where an "inhibitor of G2A, GPR4, GPR65, or OGR1" is a molecule that acts to reduce G2A, GPR4, GPR65, or OGR1 polynucleotide levels, G2A, GPR4, GPR65, or OGR1 polypeptide levels and/or G2A, GPR4, GPR65, or OGR1 protein activity. Such inhibitors include, but are not limited to, antisense polynucleotides, ribozymes, antibodies, dominant negative G2A, GPR4, GPR65, or OGR1 forms, and organic molecule inhibitors of G2A, GPR4, GPR65, or OGR1.

In preferred embodiments, G2A, GPR4, GPR65, or OGR1 levels will be reduced so as to reduce the growth or proliferation of a cancer cell with elevated G2A, GPR4, GPR65, or OGR1 levels. The proliferation of a cell refers to the rate at which the cell or population of cells divides, or to the extent to which the cell or population of cells divides or increases in number. Proliferation can reflect any of a number of factors, including the rate of cell growth and division and the rate of cell death.

The ability of any of the present compounds to affect G2A, GPR4, GPR65, or OGR1 activity can be determined based on any of a number of factors, including, but not limited to, a level of G2A, GPR4, GPR65, or OGR1 polynucleotide, e.g., mRNA or genomic DNA, the level of G2A, GPR4, GPR65, or OGR1 polypeptide, the degree of binding of a compound to a G2A, GPR4, GPR65, or OGR1 polynucleotide or polypeptide, G2A, GPR4, GPR65, or OGR1 intracellular localization, or any functional properties of G2A, GPR4, GPR65, or OGR1 protein.

Inhibitors of G2A, GPR4, GPR65, or OGR1 Polynucleotides

Antisense Polynucleotides

In certain embodiments, G2A, GPR4, GPR65, or OGR1 activity is downregulated, or entirely inhibited, by the use of antisense polynucleotide, i.e., a nucleic acid complementary to, and which can preferably hybridize specifically to, a coding mRNA nucleic acid sequence, e.g., G2A, GPR4, GPR65, or OGR1 mRNA, or a subsequence thereof. Binding of the antisense polynucleotide to the G2A, GPR4, GPR65, or OGR1 mRNA reduces the translation and/or stability of the G2A, GPR4, GPR65, or OGR1 mRNA.

In the context of this invention, antisense polynucleotides can comprise naturally-occurring nucleotides, or synthetic species formed from naturally-occurring subunits or their close homologs. Antisense polynucleotides may also have altered sugar moieties or inter-sugar linkages. Exemplary among these are the phosphorothioate and other sulfur containing species which are known for use in the art. All such analogs are comprehended by this invention so long as they function effectively to hybridize with G2A, GPR4, GPR65, or OGR1 mRNA.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Ribozymes

In addition to antisense polynucleotides, ribozymes can be used to target and inhibit transcription of cancer-associated polynucleotides such as G2A, GPR4, GPR65, or OGR1. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto et al. (1994) *Adv. in Pharmacology* 25: 289–317 for a general review of the properties of different ribozymes).

The general features of hairpin ribozymes are described, e.g., in Hampel et al. (1990) *Nucl. Acids Res.* 18: 299–304; Hampel et al. (1990) European Patent Publication No. 0 360 257; U.S. Pat. No. 5,254,678. Methods of preparing are well known to those of skill in the art (see, e.g., Wong-Staal et al., WO 94/26877; Ojwang et al. (1993) *Proc. Natl. Acad. Sci. USA* 90: 6340–6344; Yamada et al. (1994) *Human Gene Therapy* 1: 39–45; Leavitt et al. (1995) *Proc. Natl. Acad. Sci. USA* 92: 699–703; Leavitt et al. (1994) *Human Gene Therapy* 5: 1151–120; and Yamada et al. (1994) *Virology* 205: 121–126).

Inhibitors of G2A, GPR4, GPR65, or OGR1 Polypeptide Activity

G2A, GPR4, GPR65, or OGR1 activity can also be decreased by the addition of an inhibitor of the G2A, GPR4, GPR65, or OGR1 polypeptide. This can be accomplished in any of a number of ways, including by providing a dominant negative G2A, GPR4, GPR65, or OGR1 polypeptide, e.g., a form of G2A, GPR4, GPR65, or OGR1 that itself has no activity and which, when present in the same cell as a functional G2A, GPR4, GPR65, or OGR1, reduces or eliminates the G2A, GPR4, GPR65, or OGR1 activity of the functional G2A, GPR4, GPR65, or OGR1. Design of dominant negative forms is well known to those of skill and is described, e.g., in Herskowitz (1987) *Nature* 329(6136) :219–22. Also, inactive polypeptide variants (muteins) can be used, e.g., by screening for the ability to inhibit G2A, GPR4, GPR65, or OGR1 activity. Methods of making muteins are well known to those of skill (see, e.g., U.S. Pat. Nos. 5,486,463, 5,422,260, 5,116,943, 4,752,585, 4,518,504). In addition, any small molecule, e.g., any peptide, amino acid, nucleotide, lipid, carbohydrate, or any other organic or inorganic molecule can be screened for the ability to bind to or inhibit G2A, GPR4, GPR65, or OGR1 activity, as described below.

Assays for Modulators of GPCRs

A. Assays for GPCR Activity

The four GPCRs described herein and their alleles and polymorphic variants are G-protein coupled receptors that participate in signal transduction and are associated with cellular function (e.g., detection of ligands) in a variety of cells, e.g., cancer cells such as breast, colorectal, ovarian, prostate, and lung cancer cells. The activity of GPCR polypeptides can be assessed using a variety of in vitro and in vivo assays to determine functional, chemical, and physical effects, e.g., measuring ligand binding (e.g., radioactive ligand binding), second messengers (e.g., cAMP, cGMP, $IP_3$, DAG, or $Ca^{2+}$), ion flux, phosphorylation levels, transcription levels, neurotransmitter levels, and the like. Furthermore, such assays can be used to test for inhibitors and activators of a GPCR. Modulators can also be genetically altered versions of a GPCR. Screening assays of the invention are used to identify modulators that can be used as therapeutic co, e.g., antibodies to GPCRs and antagonists of GPCR activity.

The GPCR of the assay will be selected from a polypeptide having a sequence of SEQ ID NOs:2, 4, 6, or 8 or conservatively modified variant thereof. Alternatively, the GPCR of the assay will be derived from a eukaryote and include an amino acid subsequence having amino acid sequence identity to SEQ ID NOs:2, 4, 6, or 8. Generally, the amino acid sequence identity will be at least 70%, optionally at least 80%, optionally at least 90–95%. Optionally, the polypeptide of the assays will comprise a domain of a GPCR, such as an extracellular domain, transmembrane domain, cytoplasmic domain, ligand binding domain, subunit association domain, active site, and the like. Either a GPCR or a domain thereof can be covalently linked to a heterologous protein to create a chimeric protein used in the assays described herein.

Modulators of GPCR activity are tested using GPCR polypeptides as described above, either recombinant or naturally occurring. The protein can be isolated, expressed in a cell, expressed in a membrane derived from a cell, expressed in tissue or in an animal, either recombinant or naturally occurring. For example, neurons, colon cells, spleen cells, adipocytes, skin cells, transformed cells, or membranes can be used. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Gene amplification can also be examined. Furthermore, ligand-binding domains of the protein of interest can be used in vitro in soluble or solid state reactions to assay for ligand binding.

Ligand binding to GPCR, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors. Add an activator to the receptor and G protein in the absence of GTP, form a tight complex, and then screen for inhibitors by looking at dissociation of the receptor-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and $IP_3$ by phospholipase C, and in turn, for calcium mobilization by $IP_3$.

Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For a general review of GPCR signal transduction and methods of assaying signal transduction, see, e.g., *Methods in Enzymology*, vols. 237 and 238 (1994) and volume 96 (1983); Bourne et al., *Nature* 10:349:117–27 (1991); Bourne et al., Nature 348:125–32 (1990); Pitcher et al., *Annu. Rev. Biochem.* 67:653–92 (1998).

Samples or assays that are treated with a potential GPCR inhibitor or activator are compared to control samples without the test compound, to examine the extent of modulation. Control samples (untreated with activators or inhibitors) are assigned a relative GPCR activity value of 100. Inhibition of a GPCR is achieved when the GPCR activity value relative to the control is about 90%, optionally 50%, optionally 25–0%. Activation of a GPCR is achieved when the GPCR activity value relative to the control is 110%, optionally 150%, 200–500%, or 1000–2000%.

Changes in ion flux may be assessed by determining changes in polarization (i.e., electrical potential) of the cell or membrane expressing a GPCR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *P Flugers. Archiv.* 391:85 (1981). Other known assays include: radiolabeled ion flux assays and fluorescence assays using voltage-sensitive dyes (see, e.g., Vestergarrd-Bogind et al., *J. Membrane Biol.* 88:67–75 (1988); Gonzales & Tsien, *Chem. Biol.* 4:269–277 (1997); Daniel et al., *J. Pharmacol. Meth.* 25:185–193 (1991); Holevinsky et al., *J. Membrane Biology* 137:59–70 (1994)). Generally, the compounds to be tested are present in the range from 1 pM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, $IP_3$ or cAMP.

Preferred assays for G-protein coupled receptors include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha15$ and $G\alpha16$ can be used in the assay of choice (Wilkie et al., *Proc. Nat'l Acad. Sci. USA* 88:10049–10053 (1991)). Such promiscuous G-proteins allow coupling of a wide range of receptors to signal transduction pathways in heterologous cells.

Receptor activation typically initiates subsequent intracellular events, e.g., increases in second messengers such as $IP_3$, which releases intracellular stores of calcium ions. Activation of some G-protein coupled receptors stimulates the formation of inositol triphosphate ($IP_3$) through phospholipase C-mediated hydrolysis of phosphatidylinositol (Berridge & Irvine, *Nature* 312:315–21 (1984)). $IP_3$ in turn stimulates the release of intracellular calcium ion stores. Thus, a change in cytoplasmic calcium ion levels, or a change in second messenger levels such as $IP_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868–9872 (1991) and Dhallan et al., *Nature* 347:184–187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.* 270:15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3H$-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

B. Modulators

The compounds tested as modulators of GPCRs can be any small chemical compound, or a biological entity, e.g., a macromolecule such as a protein, sugar, nucleic acid or lipid. Alternatively, modulators can be genetically altered versions of a GPCR. Typically, test compounds will be small chemical molecules and peptides. Essentially any chemical compound can be used as a potential modulator or ligand in the assays of the invention, although most often compounds dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science,* 274:1520–1522 (1996) and U.S. Pat. No. 5,593,853), small organic molecule libraries (see, e.g., benzodiazepines, Baum C & EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid State and Soluble High Throughput Assays

In one embodiment the invention provide soluble assays using molecules such as a domain such as ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; a GPCR; or a cell or tissue expressing a GPCR, either naturally occurring or recombinant. In another embodiment, the invention provides solid phase based in vitro assays in a high throughput format, where the domain, chimeric molecule, GPCR, or cell or tissue expressing a GPCR is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000–20,000 different compounds is possible using the integrated systems of the invention.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the signal transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs.

For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:29). Such flexible linkers are known to persons of skill in the art. For example, poly (ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-Based Assays

Yet another assay for compounds that modulate GPCR activity involves computer assisted drug design, in which a computer system is used to generate a three-dimensional structure of GPCR based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding a GPCR polypeptide into the computer system. The amino acid sequence of the polypeptide or the nucleic acid encoding the polypeptide is selected from the group consisting of SEQ ID NOs: 2, 4 6, or 8, or SEQ ID NOs:1, 3, 5, or 7, respectively, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the GPCR protein to identify ligands that bind to GPCR. Binding affinity between the protein and ligands is determined using energy terms to determine which ligands have an enhanced probability of binding to the protein.

Computer systems are also used to screen for mutations, polymorphic variants, alleles and interspecies homologs of GPCR genes. Such mutations can be associated with disease states or genetic traits. As described above, GeneChip™ and related technology can also be used to screen for mutations, polymorphic variants, alleles and interspecies homologs.

Once the variants are identified, diagnostic assays can be used to identify patients having such mutated genes. Identification of the mutated GPCR genes involves receiving input of a first nucleic acid or amino acid sequence encoding an GPCR, selected from the group consisting of SEQ ID NOs:1, 3, 5, or 7, or SEQ ID Nos:2, 4, 6, or 8, respectively, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in GPCR genes, and mutations associated with disease states and genetic traits.

Kits

GPCRs and their homologs are a useful tool for identifying cells such as cancer cells, and for examining signal transduction. GPCR specific reagents that specifically hybridize to GPCR nucleic acids, such as GPCR probes and primers, and GPCR specific reagents that specifically bind to a GPCR protein, e.g., GPCR antibodies are used for the diagnosis and prognosis of cancer or to examine signal transduction regulation, particularly in cancer cells.

Nucleic acid assays for the presence of GPCR DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings so as to be available for hybridization within the cell while preserving the cellular morphology for subsequent interpretation and analysis (see Example I). The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, GPCR protein can be detected with the various immunoassay techniques described above. The test sample is typically compared to both a positive control (e.g., a sample expressing a recombinant GPCR) and a negative control.

The present invention also provides for kits for screening for modulators of GPCRs. Such kits can be prepared from readily available materials and reagents. For example, such kits can comprise any one or more of the following materials: a GPCR, reaction tubes, and instructions for testing GPCR activity. Optionally, the kit contains biologically active GPCR. A wide variety of kits and components can be prepared according to the present invention, depending upon the intended user of the kit and the particular needs of the user.

GPCR Functions

G2A has been identified as an oncogenic GPCR. GPR4, GPR65, and OGR1 share from about 35–50% identifity with G2A and have been identified in the present invention as oncogenic GPCRs. These four GPCRs have the ability to activate Rho GTPases. Rho GTPases can induce changes in the structure of the cytoskeleton and can contribute to transformation of a cell by stimulating mitogenesis, suppressing contact inhibition of proliferation, and overriding the requirement for cell-substrate contact (see, e.g., Zohn et al. *Oncogene* 17:1415–1438, 1998).

GPCRs are involved in the regulation of many important physiological functions and are often therapeutic targets for various diseases or conditions. Mammalian GPCRs are typically classified in three categories, class A, receptors related to rhodopsin and the adrenergic receptors, class B, receptors related to the calcitonin and parathyroid hormone receptors, and class C, receptors related to the metabotropic receptors. G2A, GPR4, GPR65, and OGR1 are class A receptors. This class is the largest and includes various amine receptor, e.g., acetylcholine (muscarinic) receptors, adrenergic receptors, dopamine receptors, histamine receptors, serotonin receptors, and octopamine receptors; peptide receptors, e.g., angiotensin, bombesin, bradykinin, endothelin, interleukin-8, chemokine, melanocortin, neuropeptide Y, neurotensin, opioid, somatostatin, tachykinin, thrombin, vasopressin, galanin, proteinase-activated, orexin, and chemokine/chemotatic factor receptors; protein hormone receptors, e.g., FSH, lutropin-choriogonadotropic hormone, and thyrotropin receptors; rhodopsin receptors; olfactory receptors; prostanoid receptors; nucleotide-like receptors, including adenosine and purinoceptors; cannabis receptors; platelet activating factor receptor; gonadotropin-releasing hormone receptor; melatonin receptor, lysosphingolipid and LPA (EDG) receptors, as well as various orphan receptors.

Class A GPCRs function in a variety of physiological processes such as vasodilation, bronchodilation, neurotransmitter signaling, stimulation of endocrine secretions, gut peristalsis, development, mitogenesis, cell proliferation, cell migration, immune system function, and oncogenesis. Accordingly, class A GPCRs can be used, for example, as probes to identify cells or tissues that exhibit dysregulation of these processes, and moreover, as screening targets to identify modulators of these processes.

Administration and Pharmaceutical Compositions

GPCR modulators can be administered directly to the mammalian subject for modulation of signal transduction in vivo, e.g., for the treatment of any of the diseases or conditions described supra. Administration is by any of the routes normally used for introducing a modulator compound into ultimate contact with the tissue to be treated. The GPCR modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, $17^{th}$ ed. 1985)).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and pre servatives. In the practice of this invention, compositions can be administered, for example, orally, topically, intravenously, intraperitoneally, intravesically or intrathecally. Optionally, the compositions are administered nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part of a prepared food or drug.

The GPCR modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

The dose administered to a patient, in the context of the present invention, should be sufficient to effect a beneficial response in the subject over time. Such doses are administered prophylactically or to an individual already suffering from the disease. The compositions are administered to a patient in an amount sufficient to elicit an effective protective or therapeutic response in the patient. An amount adequate to accomplish this is defined as "therapeutically effective dose." The dose will be determined by the efficacy of the particular GPCR modulators (e.g., GPCR antagonists and anti-GPCR antibodies) employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered in a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, GPCR modulators of the present invention can be administered at a rate determined by the LD-50 of the modulator, and the side-effects of the inhibitor at various concentrations, as applied to the mass and overall health of the subject. Administration can be accomplished via single or divided doses.

EXAMPLES

The following examples are provided by way of illustration only and not by way of limitation. Those of skill in the art will readily recognize a variety of noncritical parameters that could be changed or modified to yield essentially similar results.

Example 1

G2A, GPR4, GPR65, and OGR1 are Overexpressed in Cancer Relative to Normal

G2A, GPR4, GPR65, and OGR1 were each identified as being overexpressed in cancer. The presence of increased levels of G2A, GPR4, GPR65, and OGR1 in tumor cells was determined by analyzing mRNA expression in primary tumors.

RNA transcripts of each gene were measured by quantitative RT-PCR using the following primers and probes:

| | | |
|---|---|---|
| G2A forward: | 5' TTTGCCATCCCTCTCTCCAT 3' | [SEQ ID NO:9] |
| G2A reverse: | 5' GCTCTGCTTGATGCTCCTGAA 3' | [SEQ ID NO:10] |
| G2A probe: | 5'-Fam-ATCGCCTTCACCAACCACCGGAT-TAMRA-3' | [SEQ ID NO:11] |
| GPR4 forward: | 5' AAGATCAAGCGGCTGGCC 3' | [SEQ ID NO:12)] |
| GPR4 reverse: | 5' ACGTGATAGGGCGCAAAGC 3' | [SEQ ID NO:13] |
| GPR4 probe: | 5'-Fam-AGCCTCATCGCCATCGTGCTGGT-TAMRA-3 | [SEQ ID NO:14] |
| GPR65 forward: | 5' TCCTTGTTTTCCGTGGCTTT 3' | [SEQ ID NO:15] |
| GPR65 reverse: | 5' GGTCACCATCCTGATCTGCA 3' | [SEQ ID NO:16] |
| GPR65 probe: | 5'-Fam-CCGCACAGCTTGGTAGACTTTCCGG-TAMRA-3' | [SEQ ID NO:17] |
| OGR1 forward: | 5' AGCTGGGCGTGTACCTGTG 3' | [SEQ ID NO:18] |
| OGR1 reverse: | 5' AGAAGGGCAGCGAGCAGA 3' | [SEQ ID NO:19] |
| OGR1 probe: | 5'-Fam-ACCTGACGGTGGCCGACCTCTTCTAC-TAMRA-3' | [SEQ ID NO:20] |

Total RNA was isolated from tumor cell lines and frozen primary tumor tissues using a RNA/DNA purification kit from QIAGEN Inc or the Trizol reagent (Gibco/Life Technology). Total RNA was treated with DNAaseI (Gibco) to eliminate genomic DNA and reverse transcribed using MuLV reverse transcriptase at 48° C. for 30 min. Following the reverse transcription reaction, PCR was carried out for 40 cycles of 95° C. for 15 second and 60° C. for 1 min. The reverse transcriptase reaction coupled with PCR amplification was performed in a one-tube format using a PE/ABI 7700 Taqman machine according to the manufacturer's instruction (Perkin Elmer/ABI). The number of PCR cycles needed to cross a preset threshold, also known as Ct value, in the tumor RNA preparations and a series of normal tissue RNA preparations at various concentrations was measured for both the target probe and the β-actin probe by using a PE/ABI 7700 Taqman machine. The relative abundance of target sequence to β-actin in each sample was then calculated by statistical analyses of the Ct values of the unknown samples and the standard curve generated from the normal tissue RNA preparations at various concentrations.

G2A expression was analyzed in 49 colon, 31 breast, 18 lung, 20 ovarian, and 11 prostate tumor samples. GPR4 expression was analyzed in 29 colon, 23 breast, and 11 prostate tumors. GPR65 expression was analyzed in 11 breast, 11 ovarian, and 11 prostate tumors; OGR1 expression was analyzed in 11 breast, 11 ovarian, and 11 prostate tumors. The results are summarized in FIGS. 1–4, respectively.

Amplification of G2A

Primary tumor samples were also analyzed for amplification of G2A. DNA copy number was measured by quantitative PCR by a Taqman protocol using the PCR conditions and Taqman probe described above. Briefly, DNA was purified from primary tumors. The DNA copy number of G2A in each sample was directly measured using a pair of PCR primers and a fluorescence-labeled probe. The number of PCR cycles needed to cross a preset threshold, also known as Ct value, in the sample tumor DNA preparations and a series of normal human DNA preparations at various concentrations was measured for both the target probe and a known single-copy DNA probe by using a PE/ABI 7700 Taqman machine. The relative abundance of target sequence to the single-copy probe in each sample was then calculated by statistical analyses of the Ct values of the unknown samples and the standard curve generated from the normal human DNA preparations at various concentrations. The analysis showed that G2A was amplified from 3 to 35-fold in 8 of 112 breast tumors.

Example 2

G2A, GPR4, GPR65, and OGR1 Transform NIH3T3 Cells

The ability of the four GPCRs to induce morphological transformation was assessed in NIH3T3 cells.

Full-length cDNAs for subcloning into the retroviral expression vector were obtained using standard PCR reactions employing the following primers.

```
G2A forward:    5' AAGGATCCACCATGTGCCCAATGCTACTGAAA 3'    [SEQ ID NO:21]
G2A reverse:    5' AACCGTCGACTCAGCAGGACTCCTCAATCAG 3'     [SEQ ID NO:22]
GPR4 forward:   5' ATAGATCTCCACCATGGGCAACCACACGTGGGAG 3'  [SEQ ID NO:23]
GPR4 reverse:   5' AACCGTCGACTCATTGTGCTGGCGGCAGCAT 3'     [SEQ ID NO:24]
GPR65 forward:  5' AAGGATCCACCATGAACAGCACATGTATTGAAG 3'   [SEQ ID NO:25]
GPR65 reverse:  5' TTGTCGACCTCAAGGACCTCTAATTCCATAG 3'     [SEQ ID NO:26]
OGR1 forward:   5' AAGGATCCACCATGGGGAACATCACTGCAGAC 3'    [SEQ ID NO:27]
OGR1 reverse:   5' TTGTCGACCCGGTTGGACGGGCACCC 3'          [SEQ ID NO:28]
```

The PCR products were then subcloned into a retroviral vector for expression studies.

Figure 5:
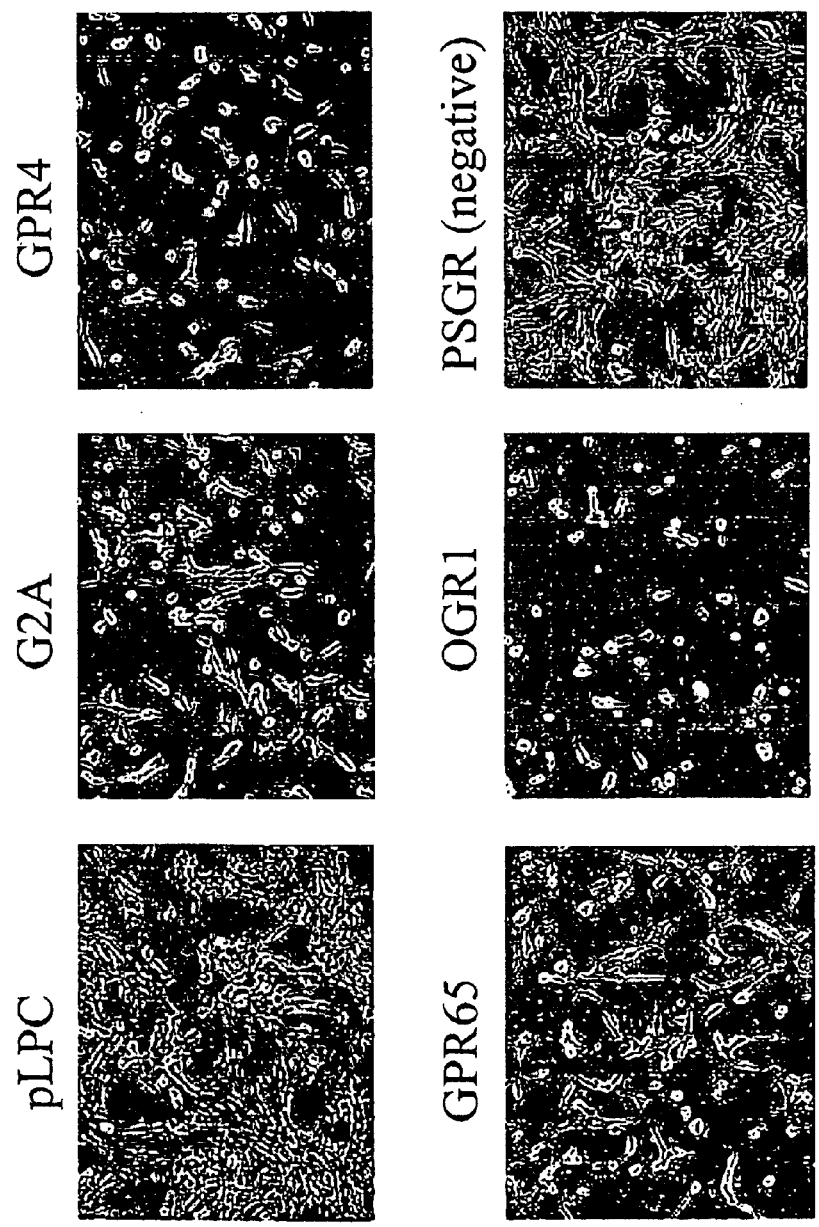
FIG. 5 sets forth data demonstrating the morphological transformation of NIH3T3 cells by GPCR2A, GPR4, GPR65, or OGR1.

NIH3T3 cells were plated at 200,00 cells/60 mm tissue culture plate in DMEM plus 10% calf serum (medium A). Twenty four hours later, cells were infected with retrovirus vectors that expressed either G2A, GPR4, OGR1, or GPR65. Twenty four hours following infection, the cells were split and subjected to selection with 2 μg/ml puromycin in medium A. Cells were then refed every 3 days and monitored for morphological transformation. G2A, GPR4, GPR65, and OGR1 each induced morphological transformation of NIH3T3 cells (FIG. 5). These results suggest that the four GPCRs are oncogenes.

Example 3

G2A, GPR4, GPR65, and OGR1 Activate Various Signaling Pathways in 293 Cells The ability of the four GPCRs to activate signaling pathways was determined using transient transfection and analysis of reporter gene activation. HEK293 cells were co-transfected with GPCR expression plasmids (the pEF6 plasmid containing cDNAs for either G2A, GPR4, OGR1 or GPR65), together with one of four reporter gene plasmids, SRE-luc, pCRE-luc, pNFAT-luc, and pFA-CREB/pFR-luc (Stratagene, La Jolla, Calif.). These reporter genes constructs include the firefly luciferase gene under the control of DNA binding elements for either Serum Response Factor (pSRE-luc), cAMP Response Element (pCRE-luc), Nuclear Factor of Activated T cell (pNFAT-luc), or the trans-reporter system with CREB as the transcription factor (pFA-CREB/pFR-luc).

Transfection was carried out with LipofectAmine 2000 reagent in OPTI-MEM medium (Gibco-BRL, Gaithersberg, Mass.) in 96-well multiwell plates. Transfection efficiency was normalized by co-transfection with the pTK-Renilla luciferase from Promega. Twenty four hours after transfection, cells were lysed and luciferase activities were measured on CLIPR (Molecular Devices, Sunnyvale, Calif.) using the Luciferase Assay Reagent from Promega (Madison, Wis.).

Figure 6:
FIG. 6 sets forth data demonstrating that G2A, GPR4, GPR65, and OGR1 activate various signaling pathways in 293 cells.
Figure 6:
Figure 6:
Figure 6:
Figure 6:
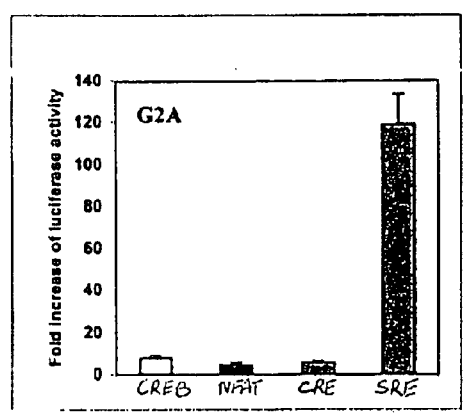
Figure 6:
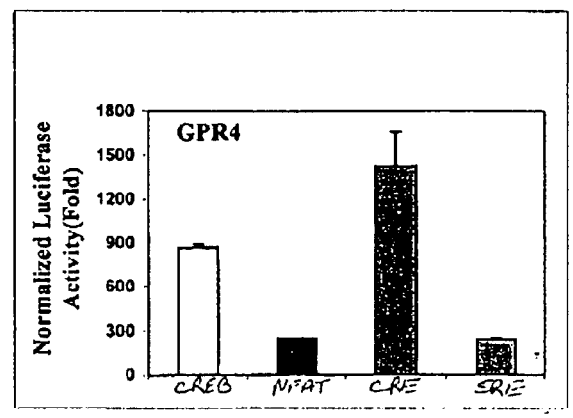
Figure 6:
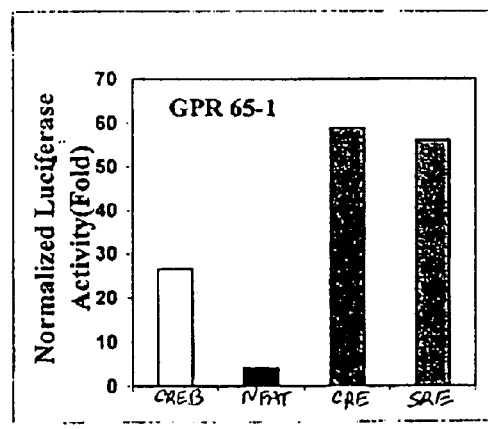
Figure 6:
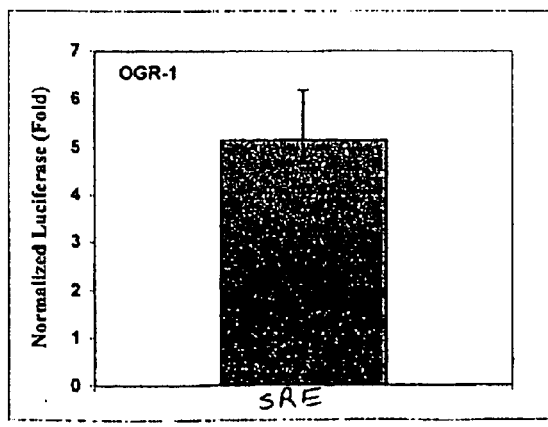

Co-transfection with the four GPCRs resulted in activation of the four reported constructs as summarized in FIG. 6.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications and patent applications cited in this specification are herein incorporated by reference as if each individual publication or patent application were specifically and individually indicated to be incorporated by reference.

GPCR Polynucleotide and Polypeptide Sequences

| SEQ ID NO:1 Human GPR4 Nucleic Acid |
|---|
| 1 ctggtgacct tacttatctc tgttgctttc tggggtccta ggaaatgcca gcactcccac |
| 61 ccacattgcc tgaactttcc aacactccct aactgcgctg tgtcctatct caacactttc |
| 121 tcatgtattt cttgtgtctt ctagaacatt cccccgccat tattacttca atatggctac |
| 181 acatacttcc taattgccct gcaaaccatc tccttctcac cattgcccag cgatgctttc |
| 241 gtctcctcca taaacactcc cggagaccaa tttttgtgtc accccatac tccctcgttg |
| 301 acacactgac tccatacata acctccttga aaaacctctt tattaatctc accatcctcc |
| 361 agacttccct cctgtcataa ttccatccct cctccaactt ttccctctca agctctgccc |
| 421 ttcccagccc agcccagcct acccaacctc atctcttccc tgtagaccac atcccaccat |
| 481 gttccoctga gcctccaagg aaggggctca gggggcccca tggcctcccg ctccctgtgg |
| 541 ccccacagcc cccgtgggcc aggggaagcg ccccagaagc cgaagtgccc accatgggca |
| 601 accacacgtg ggagggctgc cacgtggact cgcgcgtgga ccacctcttt ccgccatccc |
| 661 tctacatctt tgtcatcggc gtggggctgc ccaccaactg cctggctctg tgggcggcct |
| 721 accgccaggt gcaacagcgc aacgagctgg gcgtctacct gatgaacctc agcatcgccg |
| 781 acctgctgta catctgcacg ctgccgctgt gggtggacta cttcctgcac cacgacaact |
| 841 ggatccacgg ccccgggtcc tgcaagctct ttgggttcat cttctacacc aatatctaca |
| 901 tcagcatcgc cttcctgtgc tgcatctcgg tggaccgcta cctggctgtg gcccacccac |
| 961 tccgcttcgc ccgcctgcgc cgcgtcaaga ccgccgtggc cgtgagctcc gtggtctggg |
| 1021 ccacggagct gggcgccaac tcggcgcccc tgttccatga cgagctcttc cgagaccgct |
| 1081 acaaccacac cttctgcttt gagaagttcc ccatggaagg ctgggtggcc tggatgaacc |
| 1141 tctatcgggt gttcgtgggc ttcctcttcc cgtgggcgct catgctgctg tcgtaccggg |
| 1201 gcatcctgcg ggccgtgcgg ggcagcgtgt ccaccgagcg ccaggagaag gccaagatca |
| 1261 agcggctggc cctcagcctc atcgccatcg tgctggtctg ctttgcgccc tatcacgtgc |
| 1321 tcttgctgtc ccgcagcgcc atctacctgg gccgcccctg ggactgcggc ttcgaggagc |
| 1381 gcgtcttttc tgcataccac agctcactgg ctttcaccag cctcaactgt gtggcggacc |
| 1441 ccatcctcta ctgcctggtc aacgagggcg cccgcagcga tgtggccaag gccctgcaca |
| 1501 acctgctccg ctttctggcc agcgacaagc cccaggagat ggccaatgcc tcgctcaccc |
| 1561 tggagacccc actcacctcc aagaggaaca gcacagccaa agccatgact ggcagctggg |
| 1621 cggccactcc gccctcccag ggggaccagg tgcagctgaa gatgctgccg ccagcacaat |
| 1681 gaacccgag tggcacagaa tccccagttt tcccctctca tcccacagtc ccttctctcc |
| 1741 tggtctggtg tatgcaaatt gtatggaaaa agggctgtgt taatattcat aagaatacaa |
| 1801 gaacttagga agagtgaggt tggtgtgtca ctggtcaacc tttgtgctcc cagatcccat |
| 1861 cacagtttgg cgattgtgga gggcctcctg aaggaggaga tgagtaaata tatttttttg |
| 1921 gagacagggt ctcactgtgt tgcccaggct ggagtgcagt agtgcagtcg tggctcactg |
| 1981 cagcctccac ctcctgggct ctccagcgat cttcccacat cagcctcccg agtagctggg |

-continued

SEQ ID NO:1 Human GPR4 Nucleic Acid

```
2041 accacaaatg tgagccacca tgcctggcta attttttgtac tttttgtaga aatggagtct
2101 cactatgttt cccaggctga tcttgaactc ctgggctcaa gagatcctcc tgccttggcc
2161 tcccaaagtg ctcagattag agatgtgagc cgccatgtct ggccagataa attaagtcaa
2221 acatttggtt tccagaaaat aaagacaaat agagaaggtt agatttttt ttttccaaca
2281 agtggataaa agtctgtgac tcgggggaaa gtggaaggag aaatgcagcc gatatagagt
2341 cattatgttt gcaaagcccc tggtcataca ggccagggaa cataagaccg caattctaag
2401 tttctagata aacagcgatc tccaagtcaa gactgaggat gaagagggag aatgtcagaa
2461 ctcaagtgaa gggcaatcag ggcagactgc ctggaggagt gatgccagaa ggtttgggaa
2521 gaaggtgtgg gacaagaaga aagggtattt attcattcat tcaacagagg tttatgtagg
2581 gcactgtgct gggtggggct ggggacacaa caatgactga ggcagcctgg ccttgccttc
2641 acagggctca ccatacacaa gtaaataaaa aatatgtaat gtttggaatt gct
```

SEQ ID NO:2 Human GPR4 Protein sequence

MGNHTWEGCHVDSRVDHLFPPSLYIFVIGVGLPTNCLALWAAYRQVQQRN

ELGVYLMNLSIADLLYICTLPLWVDYFLHHDNWIHGPGSCKLFGFIFYTN

IYISIAFLCCISVDRYLAVAHPLRFARLRRVKTAVAVSSVVWATELGANS

APLFHDELFRDRYNHTFCFEKFPMEGWVAWMNLYRVFVGFLFPWALMLLS

YRGILRAVRGSVSTERQEKAKIKRLALSLIAIVLVCFAPYHVLLLSRSAI

YLGRPWDCGFEERVFSAYHSSLAFTSLNCVADPILYCLVNEGARSDVAKA

LHNLLRFLASDKPQEMANASLTLETPLTSKRNSTAKAMTGSWAATPPSQG

DQVQLKMLPPAQ"

SEQ ID NO:3 Human GPR65 Nucleic Acid sequence

```
  1 atgaacagca catgtattga agaacagcat gacctggatc actatttgtt tcccattgtt
 61 tacatctttg tgattatagt cagcattcca gccaatattg atctctgtg tgtgtctttc
121 ctgcaaccca agaaggaaag tgaactagga atttacctct tcagtttgtc actatcagat
181 ttactctatg cattaactct cccctttatgg attgattata cttggaataa agacaactgg
241 actttctctc ctgccttgtg caaggggagt gcttttctca tgtacatgaa gttttacagc
301 agcacagcat tcctcacctg cattgccgtt gatcggtatt tggctgttgt ctacccttg
361 aagttttttt tcctaaggac aagaagaatt gcactcatgg tcagcctgtc catctggata
```

SEQ ID NO:3 Human GPR65 Nucleic Acid sequence

```
421 ttggaaacca tcttcaatgc tgtcatgttg tgggaagatg aaacagttgt tgaatattgc
481 gatgccgaaa agtctaatt tactttatgc tatgacaaat acctttaga gaaatggcaa
541 atcaacctca acttgttcag gacgtgtaca ggctatgcaa tacctttggt caccatcctg
601 atctgtaacc ggaaagtcta ccaagctgtg cggcacaata agccacgga aaacaaggaa
661 aagaagagaa tcataaaact acttgtcagc atcacagtta cttttgtctt atgctttact
721 cccttttcatg tgatgttgct gattcgctgc attttagagc atgctgtgaa cttcgaagac
781 cacagcaatt ctgggaagcg aacttacaca atgtatagaa tcacggttgc attaacaagt
841 ttaaattgtg ttgctgatcc aattctgtac tgttttgtta ccgaaacagg aagatatgat
901 atgtggaata tattaaaatt ctgcactggg aggtgtaata catcacaaag acaaagaaaa
961 cgcatacttt ctgtgtctac aaaagatact atggaattag aggtccttga gtag
```

SEQ ID NO:4 Human GPR65 Protein Sequence

MNSTCIEEQHDLDHYLFPIVYIFVIIVSIPANIGSLCVSFLQPKKESELG

IYLFSLSLSDLLYALTLPLWIDYTWNKDNWTFSPALCKGSAFLMYMKFYS

STAFLTCIAVDRYLAVVYPLKFFFLRTRRIALMVSLSIWILETIFNAVML

WEDETVVEYCDAEKSNFTLCYDKYPLEKWQINLNLFRTCTGYAIPLVTIL

ICNRKVYQAVRHNKATENKEKKRIIKLLVSITVTFVLCFTPFHVMLLIRC

ILEHAVNFEDHSNSGKRTYTMYRITVALTSLNCVADPILYCFVTETGRYD

MWNILKFCTGRCNTSQRQRKRILSVSTKDTMELEVLE

SEQ ID NO:5 Human OGR1 Nucleic Acid Sequence

```
  1 atggggaaca tcactgcaga caactcctcg atgagctgta ccatcgacca taccatccac
 61 cagacgctgg ccccggtggt ctatgttacc gtgctggtgg tgggcttccc ggccaactgc
121 ctgtccctct acttcggcta cctgcagatc aaggcccgga acgagctggg cgtgtacctg
181 tgcaacctga cggtggccga cctcttctac atctgctcgc tgcccttctg gctgcagtac
241 gtgctgcagc acgacaactg gtctcacggc gacctgtcct gccaggtgtg cggcatcctc
301 ctgtacgaga acatctacat cagcgtgggc ttcctctgct gcatctccgt ggaccgctac
361 ctggctgtgg cccatcccct ccgcttccac cagttccgga ccctgaaggc ggccgtcggc
421 gtcagcgtgg tcatctgggc caaggagctg ctgaccagca tctacttcct gatgcacgag
481 gaggtcatcg aggacgagaa ccagcaccgc gtgtgctttg agcactaccc catccaggca
```

| SEQ ID NO:5 Human OGR1 Nucleic Acid Sequence |
|---|
| 541 tggcagcgcg ccatcaacta ctaccgcttc ctggtgggct tcctcttccc catctgcctg |
| 601 ctgctggcgt cctaccaggg catcctgcgc gccgtgcgcc ggagccacgg cacccagaag |
| 661 agccgcaagg accagatcca gcggctggtg ctcagcaccg tggtcatctt cctggcctgc |
| 721 ttcctgccct accacgtgtt gctgctggtg cgcagcgtct gggaggccag ctgcgacttc |
| 781 gccaagggcg ttttcaacgc ctaccacttc tccctcctgc tcaccagctt caactgcgtc |
| 841 gccgaccccg tgctctactg cttcgtcagc gagaccaccc accgggacct ggcccgcctc |
| 901 cgcggggcct gcctggcctt cctcacctgc tccaggaccg gccgggccag ggaggcctac |
| 961 ccgctgggtg cccccgaggc ctccgggaaa gcggggccc agggtgagga gcccgagctg |
| 1021 ttgaccaagc tccacccggc cttccagacc cctaactcgc agggtcggg cgggttcccc |
| 1081 acgggcaggt tggcctag |

What is claimed is:

1. A method of detecting cancer, the method comprising steps of:

(i) providing a human tissue sample that is suspected of being cancerous, and (ii) detecting an increase in the amount, relative to a control level, of a nucleic acid encoding a polypeptide comprising the amino acid sequence of SEQ ID NO:8 in the tissue sample, thereby detecting the presence of cancer.

2. The method of claim 1, wherein the detecting step comprising detecting the mRNA that encodes the polypeptide of SEQ ID NO:8.

3. The method of claim 2, wherein the mRNA is detected using an amplification reaction.

4. The method of claim 1, wherein the cancer is an epithelial cancer.

5. The method of claim 4, wherein the epithelial cancer is selected from the group consisting of breast cancer, ovarian cancer, prostate cancer, colon cancer, and lung cancer.

6. The method of claim 1, wherein the detecting step comprises detecting an increase in copy number of a gene that encodes the polypeptide, and wherein the cancer that is detected is breast cancer.

7. The method of claim 6, wherein detecting an increase in copy number of the gene comprises a PCR amplification reaction.

8. The method of claim 5, wherein the epithelial cancer is breast cancer.

9. The method of claim 5, wherein the epithelial cancer is ovarian cancer.

10. The method of claim 5, wherein the epithelial cancer is prostate cancer.

11. The method of claim 5, wherein the epithelial cancer is colon cancer.

12. The method of claim 5, wherein the epithelial cancer is lung cancer.

* * * * *

SEQUENCE LISTING

<160> NUMBER OF SEQ ID NOS: 29

<210> SEQ ID NO 1
<211> LENGTH: 2693
<212> TYPE: DNA
<213> ORGANISM: Homo sapiens
<220> FEATURE:
<223> OTHER INFORMATION: human G-protein coupled receptor 4 (GPR4)
<220> FEATURE:
<221> NAME/KEY: CDS
<222> LOCATION: (594)..(1682)
<223> OTHER INFORMATION: human G-protein coupled receptor 4 (GPR4)

<400> SEQUENCE: 1

| ctggtgacct tacttatctc tgttgctttc tggggtccta ggaaatgcca gcactcccac | 60 |
| ccacattgcc tgaactttcc aacactccct aactgcgctg tgtcctatct caacactttc | 120 |
| tcatgtattt cttgtgtctt ctagaacatt ccccgccat tattacttca atatggctac | 180 |
| acatacttcc taattgccct gcaaaccatc tccttctcac cattgcccag cgatgctttc | 240 |
| gtctcctcca taaacactcc cggagaccaa tttttgtgtc accccatac tccctcgttg | 300 |
| acacactgac tccatacata acctccttga aaaacctctt tattaatctc accatcctcc | 360 |
| agacttccct cctgtcataa ttccatccct cctccaactt ttccctctca agctctgccc | 420 |
| ttcccagccc agcccagcct acccaactc atctcttccc tgtagaccac atcccaccat | 480 |
| gttcccctga gcctccaagg aaggggctca gggggcccca tggcctcccg ctccctgtgg | 540 |
| ccccacagcc cccgtgggcc aggggaagcg ccccagaagc cgaagtgccc accatgggca | 600 |
| accacacgtg ggagggctgc cacgtggact cgcgcgtgga ccacctcttt ccgccatccc | 660 |
| tctacatctt tgtcatcggc gtggggctgc ccaccaactg cctggctctg tgggcggcct | 720 |
| accgccaggt gcaacagcgc aacgagctgg gcgtctacct gatgaacctc agcatcgccg | 780 |
| acctgctgta catctgcacg ctgccgctgt ggtggactca cttcctgcac cacgacaact | 840 |
| ggatccacgg ccccgggtcc tgcaagctct ttgggttcat cttctacacc aatatctaca | 900 |
| tcagcatcgc cttcctgtgc tgcatctcgg tggaccgcta cctggctgtg gcccaccac | 960 |
| tccgcttcgc ccgcctgcgc cgcgtcaaga ccgccgtggc cgtgagctcc gtggtctggg | 1020 |

-continued

```
ccacggagct gggcgccaac tcggcgcccc tgttccatga cgagctcttc cgagaccgct    1080
acaaccacac cttctgcttt gagaagttcc ccatggaagg ctgggtggcc tggatgaacc    1140
tctatcgggt gttcgtgggc ttcctcttcc cgtgggcgct catgctgctg tcgtaccggg    1200
gcatcctgcg ggccgtgcgg ggcagcgtgt ccaccgagcg ccaggagaag gccaagatca    1260
agcggctggc cctcagcctc atcgccatcg tgctggtctg ctttgcgccc tatcacgtgc    1320
tcttgctgtc ccgcagcgcc atctacctgg ccgcccctg ggactgcggc ttcgaggagc     1380 gcgtctttc tgcataccac agctcactgg ctttcaccag cctcaactgt gtggcggacc     1440
ccatcctcta ctgcctggtc aacgagggcg cccgcagcga tgtggccaag gccctgcaca    1500
acctgctccg ctttctggcc agcgacaagc cccaggagat ggccaatgcc tcgctcaccc    1560
tggagacccc actcacctcc aagaggaaca gcacagccaa agccatgact ggcagctggg    1620
cggccactcc gccctcccag ggggaccagg tgcagctgaa gatgctgccg ccagcacaat    1680
gaaccccgag tggcacagaa tccccagttt tcccctctca tcccacagtc ccttctctcc    1740
tggtctggtg tatgcaaatt gtatggaaaa agggctgtgt taatattcat aagaatacaa    1800
gaacttagga agagtgaggt tggtgtgtca ctggtcaacc tttgtgctcc cagatcccat    1860
cacagtttgg cgattgtgga gggcctcctg aaggaggaga tgagtaaata tatttttttg    1920
gagacagggt ctcactgtgt tgcccaggct ggagtgcagt agtgcagtcg tggctcactg    1980
cagcctccac ctcctgggct ctccagcgat cttcccacat cagcctcccg agtagctggg    2040
accacaaatg tgagccacca tgcctggcta attttttgtac tttttgtaga aatggagtct    2100
cactatgttt cccaggctga tcttgaactc ctgggctcaa gagatcctcc tgccttggcc    2160
tcccaaagtg ctcagattag agatgtgagc cgccatgtct ggccagataa attaagtcaa    2220
acatttggtt tccagaaaat aaagacaaat agagaaggtt agatttttt ttttccaaca     2280 agtggataaa agtctgtgac tcgggggaaa gtggaaggag aaatgcagcc gatatagagt    2340
cattatgttt gcaaagcccc tggtcataca ggccagggaa cataagaccg caattctaag    2400
tttctagata aacagcgatc tccaagtcaa gactgaggat gaagagggag aatgtcagaa    2460
ctcaagtgaa gggcaatcag gcagactgc ctggaggagt gatgccagaa ggtttgggaa     2520
gaaggtgtgg gacaagaaga aagggtattt attcattcat tcaacagagg tttatgtagg    2580
gcactgtgct gggtggggct ggggacacaa caatgactga ggcagcctgg ccttgccttc    2640
acagggctca ccatacacaa gtaaataaaa aatatgtaat gtttggaatt gct           2693
```

<210> SEQ ID NO 2
<211> LENGTH: 362
<212> TYPE: PRT
<213> ORGANISM: Homo sapiens
<220> FEATURE:
<223> OTHER INFORMATION: human G-protein coupled receptor 4 (GPR4)

<400> SEQUENCE: 2

```
Met Gly Asn His Thr Trp Glu Gly Cys His Val Asp Ser Arg Val Asp
  1               5                  10                  15

His Leu Phe Pro Pro Ser Leu Tyr Ile Phe Val Ile Gly Val Gly Leu
             20                  25                  30

Pro Thr Asn Cys Leu Ala Leu Trp Ala Ala Tyr Arg Gln Val Gln Gln
         35                  40                  45

Arg Asn Glu Leu Gly Val Tyr Leu Met Asn Leu Ser Ile Ala Asp Leu
     50                  55                  60

Leu Tyr Ile Cys Thr Leu Pro Leu Trp Val Asp Tyr Phe Leu His His
```

-continued

```
                65                  70                  75                  80
Asp Asn Trp Ile His Gly Pro Gly Ser Cys Lys Leu Phe Gly Phe Ile
                    85                  90                  95

Phe Tyr Thr Asn Ile Tyr Ile Ser Ile Ala Phe Leu Cys Cys Ile Ser
                100                 105                 110

Val Asp Arg Tyr Leu Ala Val Ala His Pro Leu Arg Phe Ala Arg Leu
            115                 120                 125

Arg Arg Val Lys Thr Ala Val Ala Val Ser Ser Val Val Trp Ala Thr
    130                 135                 140

Glu Leu Gly Ala Asn Ser Ala Pro Leu Phe His Asp Glu Leu Phe Arg
145                 150                 155                 160

Asp Arg Tyr Asn His Thr Phe Cys Phe Glu Lys Phe Pro Met Glu Gly
                165                 170                 175

Trp Val Ala Trp Met Asn Leu Tyr Arg Val Phe Val Gly Phe Leu Phe
                180                 185                 190

Pro Trp Ala Leu Met Leu Leu Ser Tyr Arg Gly Ile Leu Arg Ala Val
            195                 200                 205

Arg Gly Ser Val Ser Thr Glu Arg Gln Glu Lys Ala Lys Ile Lys Arg
    210                 215                 220

Leu Ala Leu Ser Leu Ile Ala Ile Val Leu Val Cys Phe Ala Pro Tyr
225                 230                 235                 240

His Val Leu Leu Leu Ser Arg Ser Ala Ile Tyr Leu Gly Arg Pro Trp
                245                 250                 255

Asp Cys Gly Phe Glu Glu Arg Val Phe Ser Ala Tyr His Ser Ser Leu
                260                 265                 270

Ala Phe Thr Ser Leu Asn Cys Val Ala Asp Pro Ile Leu Tyr Cys Leu
            275                 280                 285

Val Asn Glu Gly Ala Arg Ser Asp Val Ala Lys Ala Leu His Asn Leu
    290                 295                 300

Leu Arg Phe Leu Ala Ser Asp Lys Pro Gln Glu Met Ala Asn Ala Ser
305                 310                 315                 320

Leu Thr Leu Glu Thr Pro Leu Thr Ser Lys Arg Asn Ser Thr Ala Lys
                325                 330                 335

Ala Met Thr Gly Ser Trp Ala Ala Thr Pro Pro Ser Gln Gly Asp Gln
                340                 345                 350

Val Gln Leu Lys Met Leu Pro Pro Ala Gln
            355                 360
```

<210> SEQ ID NO 3
<211> LENGTH: 1014
<212> TYPE: DNA
<213> ORGANISM: Homo sapiens
<220> FEATURE:
<223> OTHER INFORMATION: human G-protein coupled receptor 65 (GPR65)
<220> FEATURE:
<221> NAME/KEY: CDS
<222> LOCATION: (1)..(1014)
<223> OTHER INFORMATION: human G-protein coupled receptor 65 (GPR65)

<400> SEQUENCE: 3

```
atgaacagca catgtattga agaacagcat gacctggatc actatttgtt tcccattgtt      60
tacatctttg tgattatagt cagcattcca gccaatattg gatctctgtg tgtgtctttc     120
ctgcaaccca agaaggaaag tgaactagga atttacctct tcagtttgtc actatcagat     180
ttactctatg cattaactct cccttttatgg attgattata cttggaataa agacaactgg     240
actttctctc ctgccttgtg caaagggagt gcttttctca tgtacatgaa gttttacagc     300
```

```
agcacagcat tcctcacctg cattgccgtt gatcggtatt tggctgttgt ctacccttg      360 aagttttttt tcctaaggac aagaagaatt gcactcatgg tcagcctgtc catctggata      420
ttggaaacca tcttcaatgc tgtcatgttg tgggaagatg aaacagttgt tgaatattgc      480
gatgccgaaa agtctaattt tactttatgc tatgacaaat acccttaga gaaatggcaa       540 atcaacctca acttgttcag gacgtgtaca ggctatgcaa tacctttggt caccatcctg      600
atctgtaacc ggaaagtcta ccaagctgtg cggcacaata agccacgga aacaaggaa        660 aagaagagaa tcataaaact acttgtcagc atcacagtta cttttgtctt atgctttact      720 cccttcatg tgatgttgct gattcgctgc attttagagc atgctgtgaa cttcgaagac       780
cacagcaatt ctgggaagcg aacttacaca atgtatagaa tcacggttgc attaacaagt      840
ttaaattgtg ttgctgatcc aattctgtac tgttttgtta ccgaaacagg aagatatgat      900
atgtggaata tattaaaatt ctgcactggg aggtgtaata catcacaaag acaaagaaaa      960
cgcatacttt ctgtgtctac aaaagatact atggaattag aggtccttga gtag           1014

<210> SEQ ID NO 4
<211> LENGTH: 337
<212> TYPE: PRT
<213> ORGANISM: Homo sapiens
<220> FEATURE:
<223> OTHER INFORMATION: human G-protein coupled receptor 65 (GPR65)

<400> SEQUENCE: 4

Met Asn Ser Thr Cys Ile Glu Glu Gln His Asp Leu Asp His Tyr Leu
 1               5                  10                  15

Phe Pro Ile Val Tyr Ile Phe Val Ile Val Ser Ile Pro Ala Asn
             20                  25                  30

Ile Gly Ser Leu Cys Val Ser Phe Leu Gln Pro Lys Lys Glu Ser Glu
         35                  40                  45

Leu Gly Ile Tyr Leu Phe Ser Leu Ser Leu Leu Tyr Ala
     50                  55                  60

Leu Thr Leu Pro Leu Trp Ile Asp Tyr Thr Trp Asn Lys Asp Asn Trp
 65                  70                  75                  80

Thr Phe Ser Pro Ala Leu Cys Lys Gly Ser Ala Phe Leu Met Tyr Met
                 85                  90                  95

Lys Phe Tyr Ser Ser Thr Ala Phe Leu Thr Cys Ile Ala Val Asp Arg
            100                 105                 110

Tyr Leu Ala Val Val Tyr Pro Leu Lys Phe Phe Leu Arg Thr Arg
        115                 120                 125

Arg Ile Ala Leu Met Val Ser Leu Ser Ile Trp Ile Leu Glu Thr Ile
    130                 135                 140

Phe Asn Ala Val Met Leu Trp Glu Asp Glu Thr Val Glu Tyr Cys
145                 150                 155                 160

Asp Ala Glu Lys Ser Asn Phe Thr Leu Cys Tyr Asp Lys Tyr Pro Leu
                165                 170                 175

Glu Lys Trp Gln Ile Asn Leu Asn Leu Phe Arg Thr Cys Thr Gly Tyr
            180                 185                 190

Ala Ile Pro Leu Val Thr Ile Leu Ile Cys Asn Arg Lys Val Tyr Gln
        195                 200                 205

Ala Val Arg His Asn Lys Ala Thr Glu Asn Lys Glu Lys Lys Arg Ile
    210                 215                 220

Ile Lys Leu Leu Val Ser Ile Thr Val Thr Phe Val Leu Cys Phe Thr
225                 230                 235                 240
```

-continued

```
Pro Phe His Val Met Leu Leu Ile Arg Cys Ile Leu Glu His Ala Val
                245                 250                 255

Asn Phe Glu Asp His Ser Asn Ser Gly Lys Arg Thr Tyr Thr Met Tyr
            260                 265                 270

Arg Ile Thr Val Ala Leu Thr Ser Leu Asn Cys Val Ala Asp Pro Ile
        275                 280                 285

Leu Tyr Cys Phe Val Thr Glu Thr Gly Arg Tyr Asp Met Trp Asn Ile
    290                 295                 300

Leu Lys Phe Cys Thr Gly Arg Cys Asn Thr Ser Gln Arg Gln Arg Lys
305                 310                 315                 320

Arg Ile Leu Ser Val Ser Thr Lys Asp Thr Met Glu Leu Glu Val Leu
                325                 330                 335

Glu
```

<210> SEQ ID NO 5
<211> LENGTH: 1098
<212> TYPE: DNA
<213> ORGANISM: Homo sapiens
<220> FEATURE:
<223> OTHER INFORMATION: human G-protein coupled receptor 68
      (GPR68, OGR1)
<220> FEATURE:
<221> NAME/KEY: CDS
<222> LOCATION: (1)..(1098)
<223> OTHER INFORMATION: human G-protein coupled receptor 68
      (GPR68, OGR1)

<400> SEQUENCE: 5

```
atgggaaaca tcactgcaga caactcctcg atgagctgta ccatcgacca taccatccac      60
cagacgctgg ccccggtggt ctatgttacc gtgctggtgg tgggcttccc ggccaactgc     120
ctgtccctct acttcggcta cctgcagatc aaggcccgga cgagctgggc cgtgtacctg     180
tgcaacctga cggtggccga cctcttctac atctgctcgc tgcccttctg gctgcagtac     240
gtgctgcagc acgacaactg gtctcacggc gacctgtcct gccaggtgtg cggcatcctc     300
ctgtacgaga acatctacat cagcgtgggc ttcctctgct gcatctccgt ggaccgctac     360
ctggctgtgg cccatcccct ccgcttccac cagttccgga ccctgaaggc ggccgtcggc     420
gtcagcgtgg tcatctgggc caaggagctg ctgaccagca tctacttcct gatgcacgag     480
gaggtcatcg aggacgagaa ccagcaccgc gtgtgctttg agcactaccc catccaggca     540
tggcagcgcg ccatcaacta ctaccgcttc tggtgggct tcctcttccc catctgcctg     600
ctgctggcgt cctaccaggg catcctgcgc gccgtgcgcc ggagccacgg cacccagaag     660
agccgcaagg accagatcca gcggctggtg ctcagcaccg tggtcatctt cctggcctgc     720
ttcctgccct accacgtgtt gctgctggtg cgcagcgtct gggaggccag ctgcgacttc     780
gccaagggcg ttttcaacgc ctaccacttc ccctcctgc tcaccagctt caactgcgtc     840
gccgaccccg tgctctactg cttcgtcagc gagaccaccc accgggacct ggcccgcctc     900
cgcggggcct gcctggcctt cctcacctgc tccaggaccg gccgggccag ggaggcctac     960
ccgctgggtg ccccgaggc ctccgggaaa agcggggccc aggtgagga gcccgagctg    1020
ttgaccaagc tccacccggc cttccagacc cctaactcgc cagggtcggg cgggttcccc    1080
acgggcaggt tggcctag                                                  1098
```

<210> SEQ ID NO 6
<211> LENGTH: 365
<212> TYPE: PRT

<213> ORGANISM: Homo sapiens
<220> FEATURE:
<223> OTHER INFORMATION: human G-protein coupled receptor 68
      (GPR68, OGR1)

<400> SEQUENCE: 6

```
Met Gly Asn Ile Thr Ala Asp Asn Ser Ser Met Ser Cys Thr Ile Asp
 1               5                  10                  15
His Thr Ile His Gln Thr Leu Ala Pro Val Val Tyr Val Thr Val Leu
            20                  25                  30
Val Val Gly Phe Pro Ala Asn Cys Leu Ser Leu Tyr Phe Gly Tyr Leu
        35                  40                  45
Gln Ile Lys Ala Arg Asn Glu Leu Gly Val Tyr Leu Cys Asn Leu Thr
    50                  55                  60
Val Ala Asp Leu Phe Tyr Ile Cys Ser Leu Pro Phe Trp Leu Gln Tyr
65                  70                  75                  80
Val Leu Gln His Asp Asn Trp Ser His Gly Asp Leu Ser Cys Gln Val
                85                  90                  95
Cys Gly Ile Leu Leu Tyr Glu Asn Ile Tyr Ile Ser Val Gly Phe Leu
            100                 105                 110
Cys Cys Ile Ser Val Asp Arg Tyr Leu Ala Val Ala His Pro Phe Arg
        115                 120                 125
Phe His Gln Phe Arg Thr Leu Lys Ala Ala Val Gly Val Ser Val Val
    130                 135                 140
Ile Trp Ala Lys Glu Leu Leu Thr Ser Ile Tyr Phe Leu Met His Glu
145                 150                 155                 160
Glu Val Ile Glu Asp Glu Asn Gln His Arg Val Cys Phe Glu His Tyr
                165                 170                 175
Pro Ile Gln Ala Trp Gln Arg Ala Ile Asn Tyr Tyr Arg Phe Leu Val
            180                 185                 190
Gly Phe Leu Phe Pro Ile Cys Leu Leu Leu Ala Ser Tyr Gln Gly Ile
        195                 200                 205
Leu Arg Ala Val Arg Arg Ser His Gly Thr Gln Lys Ser Arg Lys Asp
    210                 215                 220
Gln Ile Gln Arg Leu Val Leu Ser Thr Val Val Ile Phe Leu Ala Cys
225                 230                 235                 240
Phe Leu Pro Tyr His Val Leu Leu Leu Val Arg Ser Val Trp Glu Ala
                245                 250                 255
Ser Cys Asp Phe Ala Lys Gly Val Phe Asn Ala Tyr His Phe Ser Leu
            260                 265                 270
Leu Leu Thr Ser Phe Asn Cys Val Ala Asp Pro Val Leu Tyr Cys Phe
        275                 280                 285
Val Ser Glu Thr Thr His Arg Asp Leu Ala Arg Leu Arg Gly Ala Cys
    290                 295                 300
Leu Ala Phe Leu Thr Cys Ser Arg Thr Gly Arg Ala Arg Glu Ala Tyr
305                 310                 315                 320
Pro Leu Gly Ala Pro Glu Ala Ser Gly Lys Ser Gly Ala Gln Gly Glu
                325                 330                 335
Glu Pro Glu Leu Leu Thr Lys Leu His Pro Ala Phe Gln Thr Pro Asn
            340                 345                 350
Ser Pro Gly Ser Gly Gly Phe Pro Thr Gly Arg Leu Ala
        355                 360                 365
```

<210> SEQ ID NO 7
<211> LENGTH: 2588

```
<212> TYPE: DNA
<213> ORGANISM: Homo sapiens
<220> FEATURE:
<223> OTHER INFORMATION: human G-protein coupled receptor G2A
<220> FEATURE:
<221> NAME/KEY: CDS
<222> LOCATION: (901)..(2043)
<223> OTHER INFORMATION: human G-protein coupled receptor G2A
<220> FEATURE:
<221> NAME/KEY: modified_base
<222> LOCATION: (1)..(2588)
<223> OTHER INFORMATION: n = g, a, c or t

<400> SEQUENCE: 7
```

| | | | | | |
|---|---|---|---|---|---|
| gggaggggtg | cgaggctagc | cacgcaggcg | gggccctggg | tcattttaaa | ctctcagagt | 60 |
| gaacgtcttg | ataggaccga | caagacgcat | gacatgtact | tagatagctt | atcttagagc | 120 |
| cacactgaga | ttggaacccg | caaaatatgc | cagggaggaa | ggtgagcaag | ggacacgaca | 180 |
| ctcacccgga | taaacccaac | aagcgcagcg | aggctgtggg | gaaaccggan | ccctgcacac | 240 |
| cgccggggga | aggtgggccn | ccgccaccac | cgtggaagaa | cagcgcggan | gcaccccacg | 300 |
| agatgagacg | gaactgccgt | gagatccagc | aatnccnact | gtgggtctga | cccaggatan | 360 |
| cggaaagcag | ggacgtgaac | agccctcctc | atgttcttga | caccgtcatt | ctcagcagct | 420 |
| cagctaaggc | acagaggcag | ccgagcgtct | gtcagcagag | tcgtggctga | gcagaacacg | 480 |
| ccacacgcca | cacgccacac | gccacacgtg | caggattgct | caagatggaa | gggcacagtg | 540 |
| gaatatatat | atatatttat | attttttggcg | agaccctgga | ggacacactg | aatacaatgg | 600 |
| aataccatcc | cgcctttgaa | aggaagggaa | atcctggcac | acgctgcaac | aggagggagc | 660 |
| ttgaggacac | tgtggtgagt | ggagcacgtg | agacacggaa | ggacacacgc | tgaagacacg | 720 |
| cagagatgcc | cacccacgtg | gggaggtgac | agggagccc | agcgcacaga | gacaaagtgg | 780 |
| aatggaggcc | tgggggctgg | gagcaaatgc | ggagcgagtg | cttcctgggg | cagagtctcc | 840 |
| gtttgggaag | atgagaaggt | tctgccgacg | gatgctggcg | atggttgcag | aagaatgtga | 900 |
| atgtgcccaa | tgctactgaa | aaacggttac | aatggaaacg | ccaccccagt | gaccaccact | 960 |
| gccccgtggg | cctccctggg | cctctccgcc | aagacctgca | caacgtgtc | cttcgaagag | 1020 |
| agcaggatag | tcctggtcgt | ggtgtacagc | gcggtgtgca | cgctgggggt | gccggccaac | 1080 |
| tgcctgactg | cgtggctggc | gctgctgcag | gtactgcagg | gcaacgtgct | ggccgtctac | 1140 |
| ctgctctgcc | tggcactctg | cgagctgctg | tacacaggca | cgctgccact | ctgggtcatc | 1200 |
| tatatccgca | accagcaccg | ctggacccta | ggcctgctgg | cctgcaaggt | gaccgcctac | 1260 |
| atcttcttct | gcaacatcta | cgtcagcatc | ctcttcctgt | gctgcatctc | ctgcgaccgc | 1320 |
| ttcgtggccg | tggtgtacgc | gctggagagt | cggggccgcc | gccgccggag | gaccgccatc | 1380 |
| ctcatctccg | cctgcatctt | catcctcgtc | gggatcgttc | actaccggt | gttccagacg | 1440 |
| gaagacaagg | agacctgctt | tgacatgctg | cagatggaca | gcaggattgc | cgggtactac | 1500 |
| tacgccaggt | tcaccgttgg | ctttgccatc | cctctctcca | tcatcgcctt | caccaaccac | 1560 |
| cggatttttca | ggagcatcaa | gcagagcatg | ggcttaagcg | ctgcccagaa | ggccaaggtg | 1620 |
| aagcactcgg | ccatcgcggt | ggttgtcatc | ttcctagtct | gcttcgcccc | gtaccacctg | 1680 |
| gttctcctcg | tcaaagccgc | tgccttttcc | tactacagag | gagacaggaa | cgccatgtgc | 1740 |
| ggcttggagg | aaaggctgta | cacagcctct | gtggtgtttc | tgtgcctgtc | cacggtgaac | 1800 |
| ggcgtggctg | accccattat | ctacgtgctg | gccacggacc | attcccgcca | agaagtgtcc | 1860 |
| agaatccata | aggggtggaa | agagtggtcc | atgaagacag | acgtcaccag | gctcacccac | 1920 |

-continued

```
agcagggaca ccgaggagct gcagtcgccc gtggcccttg cagaccacta caccttctcc    1980
aggcccgtgc acccaccagg gtcaccatgc cctgcaaaga ggctgattga ggagtcctgc    2040
tgagcccact gtgtggcagg gggatggcag gttgggggtc ctggggccag caatgtggtt    2100
cctgtgcact gagcccacca gccacagtgc ccatgtcccc tctggaagac aaactaccaa    2160
tttctcgttc ctgaagccac tccctccgtg accactggcc ccangctttc ccacatggaa    2220
ggtggctgca tgccaagggg aagagcgaca cctccaggct tccgggagcc canagagcat    2280
gtggcangca gtgggcctc ttcatcatca ncctgcctgg ctggctccct tggctgtggg    2340
cangtacacc cctgctggca gaagtacctg gtggctgccc tgttcgcatc agtggcgatg    2400
actttatttg cggagcattt ctgcaagcgt tgcctggatg cggtggtgca ttgtgggccc    2460
tctgggctcc tgcctcaaaa tgtcagtgag caccatgctg gaagtcacca tcactgtggc    2520
agcgcccagg aaggcatagg gcancctacc acctccaang gggcangcgc cctcatctgg    2580
ggttgggt                                                              2588
```

<210> SEQ ID NO 8
<211> LENGTH: 380
<212> TYPE: PRT
<213> ORGANISM: Homo sapiens
<220> FEATURE:
<223> OTHER INFORMATION: human G-protein coupled receptor G2A

<400> SEQUENCE: 8

```
Met Cys Pro Met Leu Leu Lys Asn Gly Tyr Asn Gly Asn Ala Thr Pro
  1               5                  10                  15

Val Thr Thr Thr Ala Pro Trp Ala Ser Leu Gly Leu Ser Ala Lys Thr
                 20                  25                  30

Cys Asn Asn Val Ser Phe Glu Glu Ser Arg Ile Val Leu Val Val Val
             35                  40                  45

Tyr Ser Ala Val Cys Thr Leu Gly Val Pro Ala Asn Cys Leu Thr Ala
         50                  55                  60

Trp Leu Ala Leu Leu Gln Val Leu Gln Gly Asn Val Leu Ala Val Tyr
 65                  70                  75                  80

Leu Leu Cys Leu Ala Leu Cys Glu Leu Leu Tyr Thr Gly Thr Leu Pro
                 85                  90                  95

Leu Trp Val Ile Tyr Ile Arg Asn Gln His Arg Trp Thr Leu Gly Leu
            100                 105                 110

Leu Ala Cys Lys Val Thr Ala Tyr Ile Phe Phe Cys Asn Ile Tyr Val
        115                 120                 125

Ser Ile Leu Phe Leu Cys Cys Ile Ser Cys Asp Arg Phe Val Ala Val
    130                 135                 140

Val Tyr Ala Leu Glu Ser Arg Gly Arg Arg Arg Arg Thr Ala Ile
145                 150                 155                 160

Leu Ile Ser Ala Cys Ile Phe Ile Leu Val Gly Ile Val His Tyr Pro
                165                 170                 175

Val Phe Gln Thr Glu Asp Lys Glu Thr Cys Phe Asp Met Leu Gln Met
            180                 185                 190

Asp Ser Arg Ile Ala Gly Tyr Tyr Ala Arg Phe Thr Val Gly Phe
        195                 200                 205

Ala Ile Pro Leu Ser Ile Ile Ala Phe Thr Asn His Arg Ile Phe Arg
    210                 215                 220

Ser Ile Lys Gln Ser Met Gly Leu Ser Ala Ala Gln Lys Ala Lys Val
225                 230                 235                 240
```

```
Lys His Ser Ala Ile Ala Val Val Ile Phe Leu Val Cys Phe Ala
                245                 250                 255

Pro Tyr His Leu Val Leu Leu Val Lys Ala Ala Ala Phe Ser Tyr Tyr
            260                 265                 270

Arg Gly Asp Arg Asn Ala Met Cys Gly Leu Glu Glu Arg Leu Tyr Thr
        275                 280                 285

Ala Ser Val Val Phe Leu Cys Leu Ser Thr Val Asn Gly Val Ala Asp
    290                 295                 300

Pro Ile Ile Tyr Val Leu Ala Thr Asp His Ser Arg Gln Glu Val Ser
305                 310                 315                 320

Arg Ile His Lys Gly Trp Lys Glu Trp Ser Met Lys Thr Asp Val Thr
                325                 330                 335

Arg Leu Thr His Ser Arg Asp Thr Glu Glu Leu Gln Ser Pro Val Ala
                340                 345                 350

Leu Ala Asp His Tyr Thr Phe Ser Arg Pro Val His Pro Pro Gly Ser
            355                 360                 365

Pro Cys Pro Ala Lys Arg Leu Ile Glu Glu Ser Cys
370                 375                 380

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:quantitative
      RT-PCR primer G2A forward

<400> SEQUENCE: 9
tttgccatcc ctctctccat                                                   20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:quantitative
      RT-PCR primer G2A reverse

<400> SEQUENCE: 10
gctctgcttg atgctcctga a                                                 21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial
      Sequence:fluorescence-labeled G2A probe
<220> FEATURE:
<221> NAME/KEY: modified_base
<222> LOCATION: (1)
<223> OTHER INFORMATION: n = Fam-labeled a
<220> FEATURE:
<221> NAME/KEY: modified_base
<222> LOCATION: (23)
<223> OTHER INFORMATION: n = TAMRA-labeled t

<400> SEQUENCE: 11
ntcgccttca ccaaccaccg gan                                               23

<210> SEQ ID NO 12
<211> LENGTH: 18
<212> TYPE: DNA
<213> ORGANISM: Artificial Sequence
```

-continued

```
<220> FEATURE:
<223> OTHER INFORMATION: Description of Artificial Sequence:quantitative
      RT-PCR primer GPR4 forward

<400> SEQUENCE: 12
aagatcaagc ggctggcc                                                    18

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:quantitative
      RT-PCR primer GPR4 reverse

<400> SEQUENCE: 13
acgtgatagg gcgcaaagc                                                   19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial
      Sequence:fluorescence-labeled GPR4 probe
<220> FEATURE:
<221> NAME/KEY: modified_base
<222> LOCATION: (1)
<223> OTHER INFORMATION: n = Fam-labeled a
<220> FEATURE:
<221> NAME/KEY: modified_base
<222> LOCATION: (23)
<223> OTHER INFORMATION: n = TAMRA-labeled t

<400> SEQUENCE: 14
ngcctcatcg ccatcgtgct ggn                                              23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:quantitative
      RT-PCR primer GPR65 forward

<400> SEQUENCE: 15
tccttgtttt ccgtggcttt                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:quantitative
      RT-PCR primer GPR65 reverse

<400> SEQUENCE: 16
ggtcaccatc ctgatctgca                                                  20

<210> SEQ ID NO 17
<211> LENGTH: 25
<212> TYPE: DNA
<213> ORGANISM: Artificial Sequence
<220> FEATURE:
<223> OTHER INFORMATION: Description of Artificial
      Sequence:fluorescence-labeled GPR65 probe
<220> FEATURE:
<221> NAME/KEY: modified_base
<222> LOCATION: (1)
```

```
<223> OTHER INFORMATION: n = Fam-labeled c
<220> FEATURE:
<221> NAME/KEY: modified_base
<222> LOCATION: (25)
<223> OTHER INFORMATION: n = TAMRA-labeled g

<400> SEQUENCE: 17
ncgcacagct tggtagactt tccgn                                            25

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence:quantitative
      RT-PCR primer OGR1 forward

<400> SEQUENCE: 18
agctgggcgt gtacctgtg                                                   19

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence:quantitative
      RT-PCR primer OGR1 reverse

<400> SEQUENCE: 19
agaagggcag cgagcaga                                                    18

<210> SEQ ID NO 20
<211> LENGTH: 26
<212> TYPE: DNA
<213> ORGANISM: Artificial Sequence
<220> FEATURE:
<223> OTHER INFORMATION: Description of Artificial
      Sequence:fluorescence-labeled OGR1 probe
<220> FEATURE:
<221> NAME/KEY: modified_base
<222> LOCATION: (1)
<223> OTHER INFORMATION: n = Fam-labeled a
<220> FEATURE:
<221> NAME/KEY: modified_base
<222> LOCATION: (26)
<223> OTHER INFORMATION: n = TAMRA-labeled c

<400> SEQUENCE: 20
ncctgacggt ggccgacctc ttctan                                           26

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence:PCR primer
      G2A forward

<400> SEQUENCE: 21
aaggatccac catgtgccca atgctactga aa                                    32

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:PCR primer
      G2A reverse
```

<400> SEQUENCE: 22
aaccgtcgac tcagcaggac tcctcaatca g                31

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence:PCR primer
    GPR4 forward

<400> SEQUENCE: 23
atagatctcc accatgggca accacacgtg ggag             34

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:PCR primer
    GPR4 reverse

<400> SEQUENCE: 24
aaccgtcgac tcattgtgct ggcggcagca t                31

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence:PCR primer
    GPR65 forward

<400> SEQUENCE: 25
aaggatccac catgaacagc acatgtattg aag              33

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence:PCR primer
    GPR65 reverse

<400> SEQUENCE: 26
ttgtcgacct caaggacctc taattccata g                31

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence:PCR primer
    OGR1 forward

<400> SEQUENCE: 27
aaggatccac catggggaac atcactgcag ac               32

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence:PCR primer
    OGR1 reverse

<400> SEQUENCE: 28

-continued ttgtcgaccc ggttggacgg gcaccc    26

<210> SEQ ID NO 29
<211> LENGTH: 200
<212> TYPE: PRT
<213> ORGANISM: Artificial Sequence
<220> FEATURE:
<223> OTHER INFORMATION: Description of Artificial Sequence:poly-Gly
      flexible linker
<220> FEATURE:
<221> NAME/KEY: MOD_RES
<222> LOCATION: (6)..(200)
<223> OTHER INFORMATION: Gly at positions 6-200 may be present or absent

<400> SEQUENCE: 29

Gly Gly Gly Gly Gly Gly Gly Gly Gly Gly Gly Gly Gly Gly Gly
  1               5                  10                  15
Gly Gly Gly Gly Gly Gly Gly Gly Gly Gly Gly Gly Gly Gly Gly
             20                  25                  30
Gly Gly Gly Gly Gly Gly Gly Gly Gly Gly Gly Gly Gly Gly Gly
         35                  40                  45
Gly Gly Gly Gly Gly Gly Gly Gly Gly Gly Gly Gly Gly Gly Gly
     50                  55                  60
Gly Gly Gly Gly Gly Gly Gly Gly Gly Gly Gly Gly Gly Gly Gly
 65                  70                  75                  80
Gly Gly Gly Gly Gly Gly Gly Gly Gly Gly Gly Gly Gly Gly Gly
                 85                  90                  95
Gly Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Gly Gly
        115                 120                 125
Gly Gly Gly Gly Gly Gly Gly Gly Gly Gly Gly Gly Gly Gly Gly
    130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly
                165                 170                 175
Gly Gly Gly Gly Gly Gly Gly Gly Gly Gly Gly Gly Gly Gly Gly
            180                 185                 190
Gly Gly Gly Gly Gly Gly Gly Gly
        195                 200

| SEQ ID NO:7 Human G2A Nucleic Acid Sequence |
| --- |
| 1 gggaggggtg cgaggctagc cacgcaggcg gggccctggg tcattttaaa ctctcagagt |
| 61 gaacgtcttg ataggaccga caagacgcat gacatgtact tagatagctt atcttagagc |
| 121 cacactgaga ttggaacccg caaaatatgc cagggaggaa ggtgagcaag ggacacgaca |
| 181 ctcacccgga taaacccaac aagcgcagcg aggctgtggg gaaaccggan ccctgcacac |
| 241 cgccggggga aggtgggccn ccgccaccac cgtggaagaa cagcgcggan gcaccccacg |
| 301 agatgagacg gaactgccgt gagatccagc aatncdnact gtgggtctga cccaggatan |
| 361 cggaaagcag gacgtgaac agccctcctc atgttcttga caccgtcatt ctcagcagct |
| 421 cagctaaggc acagaggcag ccgagcgtct gtcagcagag tcgtggctga gcagaacacg |

-continued

| SEQ ID NO:7 Human G2A Nucleic Acid Sequence |
|---|
| 481 ccacacgcca cacgccacac gccacacgtg caggattgct caagatggaa gggcacagtg |
| 541 gaatatatat atatatttat attttttggcg agaccctgga ggacacactg aatacaatgg |
| 601 aataccatcc cgcctttgaa aggaagggaa atcctggcac acgctgcaac aggagggagc |
| 661 ttgaggacac tgtggtgagt ggagcacgtg agacacggaa ggacacacgc tgaagacacg |
| 721 cagagatgcc cacccacgtg gggaggtgac aggggagccc agcgcacaga gacaaagtgg |
| 781 aatggaggcc tgggggctgg gagcaaatgc ggagcgagtg cttcctgggg cagagtctcc |
| 841 gtttgggaag atgagaaggt tctgccgacg gatgctggcg atggttgcag aagaatgtga |
| 901 atgtgcccaa tgctactgaa aaacggttac aatggaaacg ccacccagt gaccaccact |
| 961 gccccgtggg cctccctggg cctctccgcc aagacctgca caacgtgtc cttcgaagag |
| 1021 agcaggatag tcctggtcgt ggtgtacagc gcggtgtgca cgctgggggt gccggccaac |
| 1081 tgcctgactg cgtggctggc gctgctgcag gtactgcagg gcaacgtgct ggccgtctac |
| 1141 ctgctctgcc tggcactctg cgagctgctg tacacaggca cgctgccact ctgggtcatc |
| 1201 tatatccgca accagcaccg ctggacccta ggcctgctgg cctgcaaggt gaccgcctac |
| 1261 atcttcttct gcaacatcta cgtcagcatc ctcttcctgt gctgcatctc ctgcgaccgc |
| 1321 ttcgtggccg tggtgtacgc gctggagagt cggggccgcc gccgccggag gaccgccatc |
| 1381 ctcatctccg cctgcatctt catcctcgtc gggatcgttc actacccggt gttccagacg |
| 1441 gaagacaagg agacctgctt tgacatgctg cagatggaca gcaggattgc cgggtactac |
| 1501 tacgccaggt tcaccgttgg ctttgccatc cctctctcca tcatcgcctt caccaaccac |
| 1561 cggatttttca ggagcatcaa gcagagcatg ggcttaagcg ctgcccagaa ggccaaggtg |
| 1621 aagcactcgg ccatcgcggt ggttgtcatc ttcctagtct gcttcgcccc gtaccacctg |
| 1681 gttctcctcg tcaaagccgc tgccttttcc tactacagag agacaggaa cgccatgtgc |
| 1741 ggcttggagg aaaggctgta cacagcctct gtggtgtttc tgtgcctgtc cacggtgaac |
| 1801 ggcgtggctg accccattat ctacgtgctg gccacggacc attcccgcca agaagtgtcc |
| 1861 agaatccata aggggtggaa agagtggtcc atgaagacag acgtcaccag gctcacccac |
| 1921 agcagggaca ccgaggagct gcagtcgccc gtggcccttg cagaccacta caccttctcc |
| 1981 aggcccgtgc acccaccagg gtcaccatgc cctgcaaaga ggctgattga ggagtcctgc |
| 2041 tgagcccact gtgtggcagg gggatggcag gttgggggtc ctggggccag caatgtggtt |
| 2101 cctgtgcact gagcccacca gccacagtgc ccatgtcccc tctggaagac aaactaccaa |
| 2161 tttctcgttc ctgaagccac tccctccgtg accactggcc ccangctttc ccacatggaa |
| 2221 ggtggctgca tgccaagggg aagagcgaca cctccaggct tccgggagcc canagagcat |
| 2281 gtggcangca gtggggcctc ttcatcatca ncctgcctgg ctggctccct ggctgtggg |
| 2341 cangtacacc cctgctggca gaagtacctg gtggctgccc tgttcgcatc agtggcgatg |
| 2401 actttatttg cggagcattt ctgcaagcgt tgcctggatg cggtggtgca ttgtgggccc |
| 2461 tctgggctcc tgcctcaaaa tgtcagtgag caccatgctg gaagtcacca tcactgtggc |
| 2521 agcgcccagg aaggcatagg gcancctacc acctccaang gggcangcgc cctcatctgg |
| 2581 ggttgggt |

```
SEQ ID NO:8 Human G2A Protein Sequence

MCPMLLKNGYNGNATPVTTTAPWASLGLSAKTCNNVSFEESRIVLVVVYS

AVCTLGVPANCLTAWLALLQVLQGNVLAVYLLCLALCELLYTGTLPLWVI

YIRNQHRWTLGLLACKVTAYIFFCNIYVSILFLCCISCDRFVAVVYALES

RGRRRRRTAILISACIFILVGIVHYPVFQTEDKETCFDMLQMDSRIAGYY

YARFTVGFAIPLSIIAFTNHRIFRSIKQSMGLSAAQKAKVKHSAIAVVVI

FLVCFAPYHLVLLVKAAAFSYYRGDRNAMCGLEERLYTASVVFLCLSTVN

GVADPIIYVLATDHSRQEVSRIHKGWKEWSMKTDVTRLTHSRDTEELQSP

VALADHYTFSRPVHPPGSPCPAKRLIEESC
```

```
SEQ ID NO:6 Human OGR1 Protein Sequence

MGNITADNSSMSCTIDHTIHQTLAPVVYVTVLVVGFPANCLSLYFGYLQI

KARNELGVYLCNLTVADLFYICSLPFWLQYVLQHDNWSHGDLSCQVCGIL

LYENIYISVGFLCCISVDRYLAVAHPFRFHQFRTLKAAVGVSVVIWAKEL

LTSIYFLMHEEVIEDENQHRVCFEHYPIQAWQRAINYYRFLVGFLFPICL

LLASYQGILRAVRRSHGTQKSRKDQIQRLVLSTVVIFLACFLPYHVLLLV

RSVWEASCDFAKGVFNAYHFSLLLTSFNCVADPVLYCFVSETTHRDLARL

RGACLAFLTCSRTGRAREAYPLGAPEASGKSGAQGEEPELLTKLHPAFQT

PNSPGSGGFPTGRLA
```